United States Patent [19]
Kiefer et al.

[11] Patent Number: 5,770,443
[45] Date of Patent: Jun. 23, 1998

[54] APOPTOSIS-MODULATING PROTEINS, DNA ENCODING THE PROTEINS AND METHODS OF USE THEREOF

[75] Inventors: Michael C. Kiefer, Clayton; Philip J. Barr, Berkeley, both of Calif.

[73] Assignee: LXR Biotechnology Inc., Richmond, Calif.

[21] Appl. No.: 471,058

[22] Filed: Jun. 6, 1995

Related U.S. Application Data

[60] Division of Ser. No. 320,157, Oct. 7, 1994, which is a continuation-in-part of Ser. No. 160,067, Nov. 30, 1993, abandoned.

[51] Int. Cl.$^6$ .......................... C12N 15/09; C12N 15/63
[52] U.S. Cl. .................. 435/325; 435/320.1; 435/69.1; 435/172.3; 435/91.2; 536/23.1; 536/23.5; 536/24.31; 935/23; 935/78; 935/79; 935/70; 935/71
[58] Field of Search .......................... 514/44; 435/172.3, 435/69.1, 240.2, 91.2, 320.1; 536/23.1, 23.5, 24.31; 935/23, 78, 79, 70, 71

[56] References Cited

U.S. PATENT DOCUMENTS

| | | |
|---|---|---|
| 5,656,725 | 8/1997 | Chittenden et al. ................. 530/324 |
| 5,672,686 | 9/1997 | Chittenden ......................... 530/387.9 |

FOREIGN PATENT DOCUMENTS

| | | |
|---|---|---|
| WO 93/04169 | 3/1993 | WIPO . |
| WO 94/00572 | 1/1994 | WIPO . |
| WO 95/00160 | 1/1995 | WIPO . |
| WO 95/00642 | 1/1995 | WIPO . |
| WO 95/05738 | 3/1995 | WIPO . |
| WO 95/05750 | 3/1995 | WIPO . |
| WO 95/15084 | 6/1995 | WIPO . |
| WO 96/05232 | 2/1996 | WIPO . |
| WO 96/35951 | 11/1996 | WIPO . |

OTHER PUBLICATIONS

Orkin et al., Report and Recommendations of the Panel to Assess the NIH Investment in Research on Gene Therapy, Dec. 7, 1995.
Coghlan, Focus, vol. 148, pp. 14–15, Nov. 25, 1995.
Brown, "News Media, Researchers 'Oversold' Gene Therapy, Advisory Panel Says", The Washington Post, Dec. 8, 1995.
Marshall, Science, vol. 269, pp. 1050–1055, Aug. 25, 1995
Kanter et al., "Epidermal growth factor and tumor promoters prevent DNA fragmentation by different mechanisms" *Biochem. Biophys. Res. Commun.* (1984) 118:392–399.
Duke et al., "IL–2 addiction: Withdrawal of growth factor activates a suicide program in dependent T cells" *Lymphokine Res.* (1986) 5:289–299.
Tomei et al., "Inhibition of radiation–induced apoptosis in vitro by tumor promoters" *Biochem. Biophys. Res. Commun.* (1988) 155:324–331.

Kruman et al., "Apoptosis of murine BW 5147 thymoma cells induced by dexamethasone and γ–irradiation" *J. Cell. Physiol.* (1991) 148:267–273.
Ameisen et al., "Cell dysfunction and depletion in AIDS: The programmed cell death hypothesis" *Immunol. Today* (1991) 12:102–105.
Sheppard et al., "The relationship between AIDS and immunologic intolerance" *J. AIDS* (1992) 5:143–147.
Gerschenson et al., "Apoptosis: A different type of cell death" *FASEB J.* (1992) 6:2450–2455.
Cohen et al., "Apoptosis and programmed cell death in immunity" *Ann. Rev. Immunol.* (1992) 10:267–293.
Tsujimoto et al., "Cloning of the chromosome breakpoint of neoplastic B cells with the t(14;18) chromosome translocation" *Science* (1984) 226:1097–1099.
Cleary et al., "Cloning and structural analysis of cDNAs for bcl–2 and a hybrid bcl–2/immunoglobin transcript resulting from the t(14;18) translocation" *Cell* (1986) 47:19–28.
McDonnell et al., "Progression from lymphoid hyperplasia to high–grade malignant lymphoma in mice transgenic for the t(14;18)" *Nature* (1991) 349:254–256.
Edgington, "Looking death in the eye: Apoptosis and cancer research" *Biotechnol.* (1993) 11:787–792.
Sentman et al., "bcl–2 inhibits multiple forms of apoptosis but not negative selection in thymocytes" *Cell* (1991) 67:879–888.
Strasser, "bcl–2 transgene inhibits T cell death and perturbs thymic self–censorship" *Cell* (1991) 67:889–899.
Hockenbery et al., "Bcl–2 functions in an antioxidant pathway to prevent apoptosis" *Cell* (1993) 75:241–251.
Williams et al., "Molecular regulation of apoptosis: genetic controls on cell death" *Cell* (1993) 74:777–779.
Zhu et al., "Systemic gene expression after intravenous DNA delivery into adult mice" Science (1993) 261:209–211.
Veis et al., "Bcl–2–deficient mice demonstrate fulminant lymphoid apoptosis, polycystic kidneys, and hypopigmented hair" *Cell* (1993) 75:229–240.
Kiefer et al., "Molecular cloning of a new human insulin–like growth factor binding protein" *Biochem. Biophys. Res. Commun.* (1991) 176:219–225.
Sanger et al., "DNA sequencing with chain–terminating inhibitors" *Proc. Natl. Acad. Sci. USA* (1977) 74:5463–5467.
Boise et al., "bcl–x, a bcl–2–related gene that functions as a dominant regulator of apoptotic cell death" *Cell* (1993) 74:597–608.
Oltvai et al., "Bcl–2 heterodimerizes in vivo with a conserved homolog, Bax, that accelerates programed cell death" *Cell* (1993) 74:609–619.

(List continued on next page.)

Primary Examiner—Jasemine C. Chambers
Assistant Examiner—Jill D. Schmuck
Attorney, Agent, or Firm—Morrison & Foerster

[57] ABSTRACT

The present invention provides a novel family of apoptosis-modulating proteins. Nucleotide and amino acid residue sequences and methods of use thereof are also provided.

30 Claims, 17 Drawing Sheets

OTHER PUBLICATIONS

Zapf et al., "Isolation from adult human serum of four insulin–like growth factor (IGF) binding proteins and molecular cloning of one of them that is increased by IGF I administration and in extrapancreatic tumor hypoglycemia" *J. Biol. Chem.* (1990). 265:14892–14898.

Feinberg et al., "A technique for radiolabeling DNA restriction endonuclease fragments to high specific activity" *Anal. Biochem.* (1984) 137:266–267.

Chen–Levy et al., "The bcl–2 candidate proto–oncogene product is a 24–kilodalton integral–membrane protein highly expressed in lymphoid cell lines and lymphomas carrying the t(14;18) translocation" *Mol. Cell. Biol.* (1989) 9:701–710.

Jacobson et al., "Bcl–2 blocks apoptosis in cells lacking mitochondrial DNA" *Nature* (1993) 361:365–369.

Monaghan et al., "Ultrastructural localization of BCL–2 protein" *J. Histochem. Cytochem.* (1992) 40:1819–1825.

Lehrach et al., "RNA molecular weight determinations by gel electrophoresis under denaturing conditions, a critical reexamination" *Biochem.* (1977) 16:4743–4751.

Thomas, "Hybridization of denatured RNA and small DNA fragments transferred to nitrocellulose" *Proc. Natl. Acad. Sci. USA* (1980) 77:5201–5205.

Barr, "Expression of foreign genes in yeast" *Transgenesis* (1992) Murray, J.A.H., ed., Wiley & Sons, New York, pp. 55–79.

Henderson et al., "Epstein–Barr virus–coded BHRF1 protein, a viral homologue of Bcl–2, protects human B cells from programmed cell death" *Proc. Natl. Acad. Sci. USA* (1993) 90:8479–8483.

Viegas–Péquignot, "In situ hybridization to chromosomes with biotinylated probes" *In Situ Hybridization. A Practical Approach,* D.G. Wilkinson, ed., IRL Press, Oxford, pp. 137–158.

Pinkel et al., "Fluorescence in situ hybrization with human chromosome–specific libraries: Detection of trisomy 21 and translocations of chromosome 4" *Proc. Natl. Acad. Sci. USA* (1988) 85:9138–9142.

McKearn et al., "Enrichment of hematopoietic precursor cells and cloning of multipotential B–lymphocyte precursors" *Proc. Natl. Acad. Sci. USA* (1985) 82:7414–7418.

Nuñez et al., "Deregulated Bcl–2 gene expression selectively prolongs survival of growth factor–deprived hemopoietic cell lines" *J. Immunol,* (1990) 144:3602–3610.

Hockenbery et al., "Bcl–2 is an inner mitochondrial protein that blocks programmed cell death" *Nature* (1990) 34:334–336.

Cherif et al., "Ordering markers in the region of the ataxia–telangiectasia gene (11q22–q23) by fluorescence in situ hybridization (FISH) to interphase nuclei" *Hum. Genet,* (1994) 93:1–6.

Foroud et al., "Localization of an ataxia–telangiectasia locus to a 3–cM interval on chromosome 11q23: Linkage analysis of 111 families by an international consortium" *Am. J. Hum. Genet.* (1991) 49:1263–1279.

Kapp et al., "Cloning of a candidate gene for ataxia–telangiectasia group D" *Am. J. Hum. Genet,* (1992) 51:45–54.

Khati et al., "Genetic heterogeneity of autosomal dominant cerebellar ataxia type 1: Clinical and genetic analysis of 10 French families" *Neurology* (1993) 43:1131–1137.

Meyn, "Ataxia–telangiectasia, apoptosis and cellular responses to DNA damage: A model" *Cancer Genet.* (1993) 53:(Abstract No. 1529).

Orr et al., "Expansion of an unstable trinucleotide CAG repeat in spinocerebellar ataxia type 1" *Nature Genetics* (1993) 4:221–226.

Kennedy, "Prevention of carcinogenesis by protease inhibitors" *Cancer Res.* (1994) 54:1999s–2005s.

Lam et al., "Evidence that BCL-2 represses apoptosis by regulating endoplasmic reticulum–associated $Ca^{2+}$ fluxes" *Proc. Natl. Acad. Sci. USA* (1994) 91:6569–6573.

Reed et al., "Antisense–mediated inhibition of BCL2 protooncogene expression and leukemic cell growth and survival: Comparisons of phosphodiester and phosphorothioate oligodeoxynucleotides" *Cancer Res.* (1990) 50:6565–6570.

Yonehara et al., "A cell–killing monoclonal antibody (ANTI–Fas) to a cell surface antigen co–downregulated with the receptor of tumor necrosis factor" *J. Exp. Med.* (1989) 169:1747–1756.

Hickish et al., "Ultrastructural localization of BHRF1: An Epstein–Barr virus gene product which has homology with bcl–2" *Cancer Research* (1994) 54:2808–2811.

Tarodi et al., "Epstein–Barr virus BHRF1 protein protects against cell death induced by DNA–damaging agents and heterologous viral infection" *Virology* (1994) 201:404–407.

Chittenden et al., "Induction of apoptosis by the Bcl–2 homologue Bak" *Nature* (1995) 347:733–736.

Farrow et al., "Cloning of a bcl–2 homologue by interaction with adenovirus E1B 19K" *Nature* (1995) 374:731–733.

Kiefer et al., "Modulation of apoptosis by the widely distributed Bcl–2 homologue Bak" *Nature* (1995) 374:736–739.

Wyllie, "Glucocorticoid–induced thymocyte apoptosis is associated with endogenous endonuclease activation" *Nature* (1980) 284:555–556.

Lewin, R., "When Does Homology Mean Something Else?" *Science* (1987) 237:1570.

Reeck et al. "Homology in Proteins and Nucleic Acids: A Terminology Muddle and a Way Out of it" *Cell* (1987) 50: 667.

Figure 1

```
                                        Ile
EcoRI AspTrpGlyArgValValAla                              SEQ ID NO.: 1
5- AGATCTGAATTCAACTTGGGGGIC(A)GIA(G)TXGTXGC -3'  bclx 1-32
                                                         SEQ ID NO.: 2

AspTrpGlyGlyGlnGluAsnAspGlnIleTrp           SEQ ID NO.: 3
                  AGGGTIGGIGGXACXAGA(G)ACA(T)(C)TAGGT  SEQ ID NO.: 4
5'- AGATCT'AAGCTTGTCCCAICCICCXTGXTCC(T)TGA(G)ATCCA -3'  bclX 2-39
                                                         SEQ ID NO.: 5
```

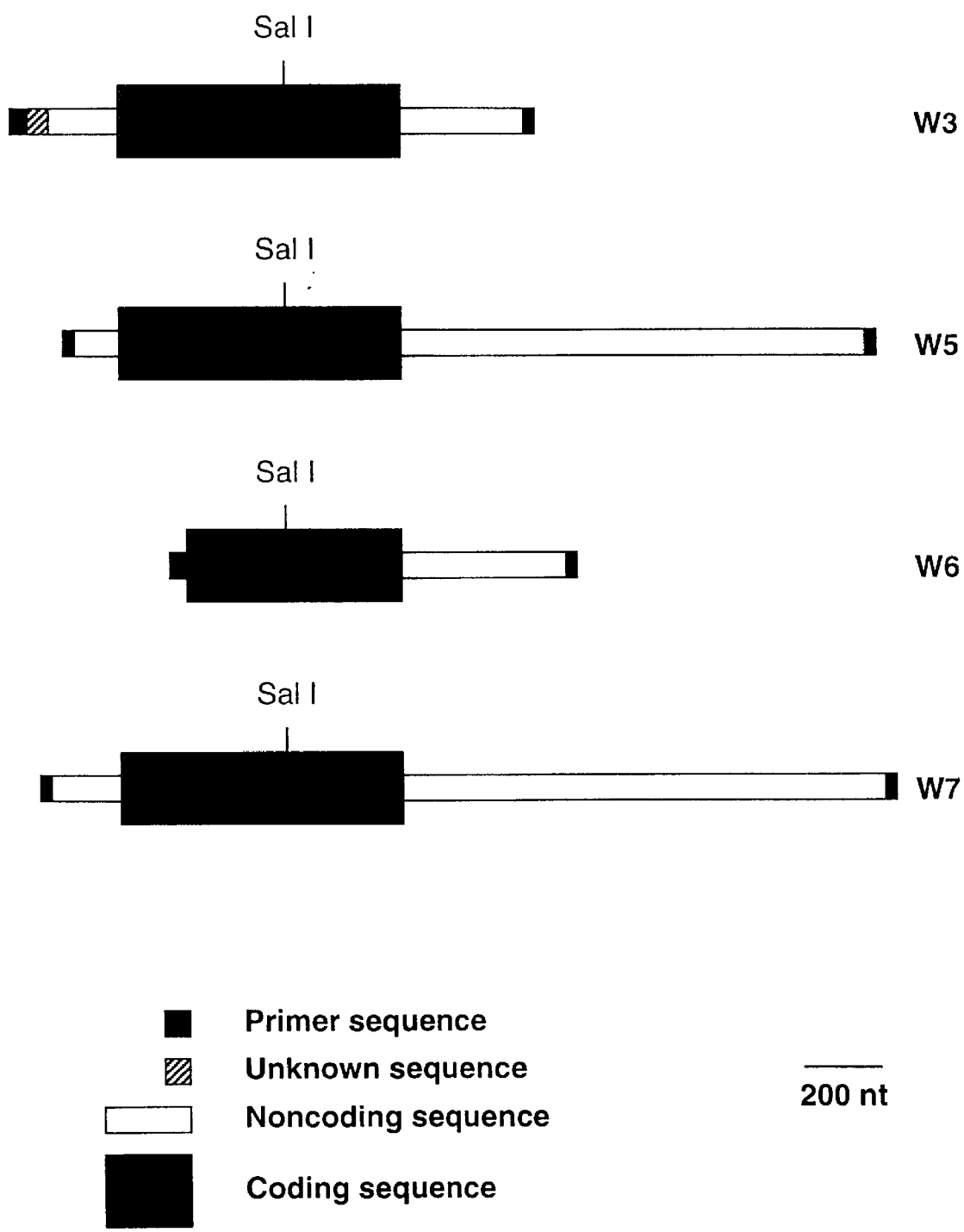

SEQ ID NO.: 6 ## Figure 3A

```
                                                              >Aha2
         10         20         30         40         50    |   60         70         80
          *          *          *          *          *          *          *          *
GAGGATCTAC AGGGGACAAG TAAAGGCTAC ATCCAGATGC CGGGAATGCA CTGACGCCCA TTCCTGGAAA CTGGGCTCCC
CTCCTAGATG TCCCCTGTTC ATTTCCGATG TAGGTCTACG GCCCTTACGT GACTGCGGGT AAGGACCTTT GACCCGAGGG

>Sma1         >BamH1
         90        100        110        120        130        140    |  150       |  160
          *          *          *          *          *          *          *          *
ACTCAGCCCC TGGGAGCAGC AGCCGCCAGC CCCTCGGACC TCCATCTCCA CCCTGCTGAG CCACCCGGGT TGGGCCAGGA
TGAGTCGGGG ACCCTCGTCG TCGGCGGTCG GGGAGCCTGG AGGTAGAGGT GGGACGACTC GGTGGGCCCA ACCCGGTCCT

>Bsa1
        170        180  |     190        200        210        220        230
          *          *          *          *          *          *          *
TCCCGGCAGG CTGATCCCGT CCTCCACTGA GACCTGAAAA ATG GCT TCG GGG CAA GGC CCA GGT CCT CCC AGG
AGGGCCGTCC GACTAGGGCA GGAGGTGACT CTGGACTTTT TAC CGA AGC CCC GTT CCG GGT CCA GGA GGG TCC
                                              M   A   S   G   Q   G   P   G   P   P   R>

240        250        260        270        280        290
          *          *          *          *          *          *
CAG GAG TGC GGA GAG CCT GCC CTG CCC TCT GCT TCT GAG GAG CAG GTA GCC CAG GAC ACA GAG GAG
GTC CTC ACG CCT CTC GGA CGG GAC GGG AGA CGA AGA CTC CTC GTC CAT CGG GTC CTG TGT CTC CTC
 Q   E   C   G   E   P   A   L   P   S   A   S   E   E   Q   V   A   Q   D   T   E   E>

300        310        320        330        340        350        360
  *          *          *          *          *          *          *
GTT TTC CGC AGC TAC GTT TTT TAC CGC CAT CAG CAG GAA CAG GAG GCT GAA GGG GTG GCT GCC CCT
CAA AAG GCG TCG ATG CAA AAA ATG GCG GTA GTC GTC CTT GTC CTC CGA CTT CCC CAC CGA CGG GGA
 V   F   R   S   Y   V   F   Y   R   H   Q   Q   E   Q   E   A   E   G   V   A   A   P>

>Nco1
        370        380        390        400    |    410        420        430
          *          *          *          *     |     *          *          *
GCC GAC CCA GAG ATG GTC ACC TTA CCT CTG CAA CCT AGC AGC ACC ATG GGG CAG GTG GGA CGG CAG
CGG CTG GGT CTC TAC CAG TGG AAT GGA GAC GTT GGA TCG TCG TGG TAC CCC GTC CAC CCT GCC GTC
 A   D   P   E   M   V   T   L   P   L   Q   P   S   S   T   M   G   Q   V   G   R   Q>

440        450        460        470        480        490
          *          *          *          *          *          *
CTC GCC ATC ATC GGG GAC GAC ATC AAC CGA CGC TAT GAC TCA GAG TTC CAG ACC ATG TTG CAG CAC
GAG CGG TAG TAG CCC CTG CTG TAG TTG GCT GCG ATA CTG AGT CTC AAG GTC TGG TAC AAC GTC GTG
 L   A   I   I   G   D   D   I   N   R   R   Y   D   S   E   F   Q   T   M   L   Q   H>

>Pst1                             >Sca1
        500 |       510        520    |    530        540        550        560
          *          *          *          *          *          *          *
CTG CAG CCC ACG GCA GAG AAT GCC TAT GAG TAC TTC ACC AAG ATT GCC ACC AGC CTG TTT GAG AGT
GAC GTC GGG TGC CGT CTC TTA CGG ATA CTC ATG AAG TGG TTC TAA CGG TGG TCG GAC AAA CTC TCA
 L   Q   P   T   A   E   N   A   Y   E   Y   F   T   K   I   A   T   S   L   F   E   S>

570        580        590        600        610        620
          *          *          *          *          *          *
GGC ATC AAT TGG GGC CGT GTG GTG GCT CTT CTG GGC TTC GGC TAC CGT CTG GCC CTA CAC GTC TAC
CCG TAG TTA ACC CCG GCA CAC CAC CGA GAA GAC CCG AAG CCG ATG GCA GAC CGG GAT GTG CAG ATG
 G   I   N   W   G   R   V   V   A   L   L   G   F   G   Y   R   L   A   L   H   V   Y>

>Sal1
630        640        650        660        670    |    680        690
  *          *          *          *          *          *          *
CAG CAT GGC CTG ACT GGC TTC CTA GGC CAG GTG ACC CGC TTC GTG GTC GAC TTC ATG CTG CAT CAC
GTC GTA CCG GAC TGA CCG AAG GAT CCG GTC CAC TGG GCG AAG CAC CAG CTG AAG TAC GAC GTA GTG
 Q   H   G   L   T   G   F   L   G   Q   V   T   R   F   V   V   D   F   M   L   H   H>

700        710        720        730        740        750        760
          *          *          *          *          *          *          *
TGC ATT GCC CGG TGG ATT GCA CAG AGG GGT GGC TGG GTG GCA GCC CTG AAC TTG GGC AAT GGT CCC
ACG TAA CGG GCC ACC TAA CGT GTC TCC CCA CCG ACC CAC CGT CGG GAC TTG AAC CCG TTA CCA GGG
 C   I   A   R   W   I   A   Q   R   G   G   W   V   A   A   L   N   L   G   N   G   P>

770        780        790        800        810        820
          *          *          *          *          *          *
ATC CTG AAC GTG CTG GTG GTT CTG GGT GTG GTT CTG TTG GGC CAG TTT GTG GTA CGA AGA TTC TTC
TAG GAC TTG CAC GAC CAC CAA GAC CCA CAC CAA GAC AAC CCG GTC AAA CAC CAT GCT TCT AAG AAG
 I   L   N   V   L   V   V   L   G   V   V   L   L   G   Q   F   V   V   R   R   F   F>
```

Figure 3B

```
                                                              >Afl2
    830        840        850        860        870        880|       890        900
     *          *          *          *          *          *          *          *
AAA TCA TGA CTCC CAAGGGTGCC CTTTGGGTCC CGGTTCAGAC CCCTGCCTGG ACTTAAGCGA AGTCTTTGCC
TTT AGT ACT GAGG GTTCCCACGG GAAACCCAGG GCCAAGTCTG GGGACGGACC TGAATTCGCT TCAGAAACGG
 K   S   *>

>Hind3
                                                  |
    910        920        930        940|       950        960        970        980
     *          *          *          *          *          *          *          *
TTCTCTGTTC CCTTGCAGGG TCCCCCCTCA AGAGTACAGA AGCTTTAGCA AGTGTGCACT CCAGCTTCGG AGGCCCTGCG
AAGAGACAAG GGAACGTCCC AGGGGGGAGT TCTCATGTCT TCGAAATCGT TCACACGTGA GGTCGAAGCC TCCGGGACGC >PstI                                                        >ApaI
                 |                                                            |
    990       1000|      1010       1020       1030       1040      1050|     1060
     *          *          *          *          *          *          *          *
TGGGGGCCAG TCAGGCTGCA GAGGCACCTC AACATTGCAT GGTGCTAGTG CCCTCTCTCT GGGCCCAGGG CTGTGGCCGT
ACCCCCGGTC AGTCCGACGT CTCCGTGGAG TTGTAACGTA CCACGATCAC GGGAGAGAGA CCCGGGTCCC GACACCGGCA 1070       1080       1090       1100       1110       1120       1130       1140
     *          *          *          *          *          *          *          *
CTCCTCCCTC AGCTCTCTGG GACCTCCTTA GCCCTGTCTG CTAGGCGCTG GGGAGACTGA TAACTTGGGG AGGCAAGAGA
GAGGAGGGAG TCGAGAGACC CTGGAGGAAT CGGGACAGAC GATCCGCGAC CCCTCTGACT ATTGAACCCC TCCGTTCTCT 1150       1160       1170       1180       1190       1200       1210       1220
     *          *          *          *          *          *          *          *
CTGGGAGCCA CTTCTCCCCA GAAAGTGTTT AACGGTTTTA GCTTTTTATA ATACCCTTGT GAGAGCCCAT TCCCACCATT
GACCCTCGGT GAAGAGGGGT CTTTCACAAA TTGCCAAAAT CGAAAAATAT TATGGGAACA CTCTCGGGTA AGGGTGGTAA >Aha2
               |
    1230       |1240      1250       1260       1270       1280       1290       1300
     *          *          *          *          *          *          *          *
CTACCTGAGG CCAGGACGTC TGGGGTGTGG GGATTGGTGG GTCTATGTTC CCCAGGATTC AGCTATTCTG GAAGATCAGC
GATGGACTCC GGTCCTGCAG ACCCCACACC CCTAACCACC CAGATACAAG GGGTCCTAAG TCGATAAGAC CTTCTAGTCG 1310       1320       1330       1340       1350       1360       1370       1380
     *          *          *          *          *          *          *          *
ACCCTAAGAG ATGGGACTAG GACCTGAGCC TGGTCCTGCC CGTCCCTAAG CATGTGTCCC AGGAGCAGGA CCTACTAGGA
TGGGATTCTC TACCCTGATC CTGGACTCGG ACCAGGACCG GCAGGGATTC GTACACAGGG TCCTCGTCCT GGATGATCCT 1390       1400       1410       1420       1430       1440       1450       1460
     *          *          *          *          *          *          *          *
GAGGGGGGCC AAGGTCCTGC TCAACTCTAC CCCTGCTCCC ATTCCTCCCT CCGGCCATAC TGCCTTTGCA GTTGGACTCT
CTCCCCCCGG TTCCAGGACG AGTTGAGATG GGGACGAGGG TAAGGAGGGA GGCCGGTATG ACGGAAACGT CAACCTGAGA 1470       1480       1490       1500       1510       1520       1530       1540
     *          *          *          *          *          *          *          *
CAGGGATTCT GGGCTTGGGG TGTGGGGTGG GGTGGAGTCG CAGACCAGAG CTGTCTGAAC TCACGTGTCA GAAGCCTCCA
GTCCCTAAGA CCCGAACCCC ACACCCCACC CCACCTCAGC GTCTGGTCTC GACAGACTTG AGTGCACAGT CTTCGGAGGT 1550       1560       1570       1580       1590       1600       1610       1620
     *          *          *          *          *          *          *          *
AGCCTGCCTC CCAAGGTCCT CTCAGTTCTC TCCCTTCCTC TCTCCTTATA GACACTTGCT CCCAACCCAT TCACTACAGG
TCGGACGGAG GGTTCCAGGA GAGTCAAGAG AGGGAAGGAG AGAGGAATAT CTGTGAACGA GGGTTGGGTA AGTGATGTCC 1630       1640       1650       1660       1670       1680       1690       1700
     *          *          *          *          *          *          *          *
TGAAGGCTCT CACCCATCCC TGGGGGCCTT GGGTGAGTGG CCTGCTAAGG CTCCTCCTTG CCCAGACTAC AGGGCTTAGG
ACTTCCGAGA GTGGGTAGGG ACCCCCGGAA CCCACTCACC GGACGATTCC GAGGAGGAAC GGGTCTGATG TCCCGAATCC 1710       1720       1730       1740       1750       1760       1770       1780
     *          *          *          *          *          *          *          *
ACTTGGTTTG TTATATCAGG GAAAAGGAGT AGGGAGTTCA TCTGGAGGGT TCTAAGTGGG AGAAGGACTA TCAACACCAC
TGAACCAAAC AATATAGTCC CTTTTCCTCA TCCCTCAAGT AGACCTCCCA AGATTCACCC TCTTCCTGAT AGTTGTGGTG >BamH1
                |
    1790       |1800      1810       1820       1830       1840       1850       1860
     *          *          *          *          *          *          *          *
TAGGAATCCC AGAGGTGGAT CCTCCCTCAT GGCTCTGGCA CAGTGTAATC CAGGGGTGTA GATGGGGAA CTGTGAATAC
ATCCTTAGGG TCTCCACCTA GGAGGGAGTA CCGAGACCGT GTCACATTAG GTCCCACAT CTACCCCTT GACACTTATG
```

Figure 3C

```
                                                          >BsaI
      1870       1880       1890       1900       1910       1920       1930       1940
        *          *          *          *         |*          *          *          *
  TTGAACTCTG TTCCCCCACC CTCCATGCTC CTCACCTGTC TAGGTCTCCT CAGGGTGGGG GGTGACAGTG CCTTCTCTAT
  AACTTGAGAC AAGGGGGTGG GAGGTACGAG GAGTGGACAG ATCCAGAGGA GTCCCACCCC CCACTGTCAC GGAAGAGATA 1950       1960       1970       1980       1990       2000       2010       2020
        *          *          *          *          *          *          *          *
  TGGCACAGCC TAGGGTCTTG GGGGTCAGGG GGGAGAAGTT CTTGATTCAG CCAAATGCAG GGAGGGGAGG CAGATGGAGC
  ACCGTGTCGG ATCCCAGAAC CCCCAGTCCC CCCTCTTCAA GAACTAAGTC GGTTTACGTC CCTCCCCTCC GTCTACCTCG 2030       2040       2050       2060       2070       2080       2090
        *          *          *          *          *          *          *
  CCATAGGCCA CCCCCTATCC TCTGAGTGTT TGGAAATAAA CTGTGCAATC CCCTCAAAAA AAAAACGGAG ATCC
  GGTATCCGGT GGGGGATAGG AGACTCACAA ACCTTTATTT GACACGTTAG GGGAGTTTTT TTTTTGCCTC TAGG
```

Figure 5A

SEQ ID NO.: 8

```
               10         20         30         40         50         60
                *          *          *          *          *          *
     TTT TAA TAT AAA TTA ATG TGC TCT ATT TAT AGA GAC AAT ACA TGA AAT ATA CTT AAT AAA
     AAA ATT ATA TTT AAT TAC ACG AGA TAA ATA TCT CTG TTA TGT ACT TTA TAT GAA TTA TTT 70         80         90        100        110        120
                *          *          *          *          *          *
     AAT TCA AAT GTT ATA GAA CTG AAA AAG ATG AAA AGT AAA AAC AAC CTA TTC CCC AGA GGT
     TTA AGT TTA CAA TAT CTT GAC TTT TTC TAC TTT TCA TTT TTG TTG GAT AAG GGG TCT CCA 130        140        150        160        170        180
                *          *          *          *          *          *
     AGC CAC TGT CCA TAG TTT CTA TTT TAG ATT CTT TCC TTT ATA CAA GAT TAT TAT AGC TTC
     TCG GTG ACA GGT ATC AAA GAT AAA ATC TAA GAA AGG AAA TAT GTT CTA ATA ATA TCG AAG 190        200        210        220        230        240
                *          *          *          *          *          *
     TAT TTT TTG GTG TAT GAA CTG TAG TCC TAG AGG ATT TTA TTA GTT ATG AGT TCT ATA ACT
     ATA AAA AAC CAC ATA CTT GAC ATC AGG ATC TCC TAA AAT AAT CAA TAC TCA AGA TAT TGA 250        260        270        280        290        300
                *          *          *          *          *          *
     AAG ATC CAT CAT CTT AGT TGC TAA GAA CGT AGA TAC TGA GAA CAT CAT TTA AAA AAA CAT
     TTC TAG GTA GTA GAA TCA ACG ATT CTT GCA TCT ATG ACT CTT GTA GTA AAT TTT TTT GTA 310        320        330        340        350        360
                *          *          *          *          *          *
     TTT TGG CTG GCA CCT CAT GAT CAC TGG AGT CTC GCG GGT CCC TCA GGC TGC ACA GGG ACA
     AAA ACC GAC CGT GGA GTA CTA GTG ACC TCA GAG CGC CCA GGG AGT CCG ACG TGT CCC TGT 370        380        390        400        410        420
                *          *          *          *          *          *
     AGT AAA GGC TAC ATC CAG ATG CTG GGA ATG CAC TGA CGC CCA TTC CTG GAA ACT GGG CTC
     TCA TTT CCG ATG TAG GTC TAC GAC CCT TAC GTG ACT GCG GGT AAG GAC CTT TGA CCC GAG 430        440        450        460        470        480
                *          *          *          *          *          *
     CCA CTC AGC CCC TGG GAG CAG CAG CCG CCA GCC CCT CGG GAC CTC CAT CTC CAC CCT GCT
     GGT GAG TCG GGG ACC CTC GTC GTC GGC GGT CGG GGA GCC CTG GAG GTA GAG GTG GGA CGA

>BamHI
              490        500|       510        520        530        540
                *          *|         *          *          *          *
     GAG CCA CCC GGG TTG GGC CAG GAT CCC GGC AGG CTG ATC CCG TCC TCC ACT GAG ACC TGA
     CTC GGT GGG CCC AAC CCG GTC CTA GGG CCG TCC GAC TAG GGC AGG AGG TGA CTC TGG ACT 550        560        570        580        590        600
                *          *          *          *          *          *
     AAA ATG GCT TCG GGG CAA GGC CCA GGT CCT CCC AGG CAG GAG TGC GGA GAG CCT GCC CTG
     TTT TAC CGA AGC CCC GTT CCG GGT CCA GGA GGG TCC GTC CTC ACG CCT CTC GGA CGG GAC
          M   A   S   G   Q   G   P   G   P   P   R   Q   E   C   G   E   P   A   L>

610        620        630        640        650        660
                *          *          *          *          *          *
     CCC TCT GCT TCT GAG GAG CAG GTA GCC CAG GAC ACA GAG GAG GTT TTC CGC AGC TAC GTT
     GGG AGA CGA AGA CTC CTC GTC CAT CGG GTC CTG TGT CTC CTC CAA AAG GCG TCG ATG CAA
      P   S   A   S   E   E   Q   V   A   Q   D   T   E   E   V   F   R   S   Y   V>

670        680        690        700        710        720
                *          *          *          *          *          *
     TTT TAC CAC CAT CAG CAG GAA CAG GAG GCT GAA GGG GCG GCT GCC CCT GCC GAC CCA GAG
     AAA ATG GTG GTA GTC GTC CTT GTC CTC CGA CTT CCC CGC CGA CGG GGA CGG CTG GGT CTC
      F   Y   H   H   Q   Q   E   Q   E   A   E   G   A   A   A   P   A   D   P   E>
```

Figure 5B

```
              730         740         750   >NcoI  760         770         780
               *           *           *   |       *           *           *
ATG GTC ACC TTA CCT CTG CAA CCT AGC AGC ACC ATG GGG CAG GTG GGA CGG CAG CTC GCC
TAC CAG TGG AAT GGA GAC GTT GGA TCG TCG TGG TAC CCC GTC CAC CCT GCC GTC GAG CGG
 M   V   T   L   P   L   Q   P   S   S   T   M   G   Q   V   G   R   Q   L   A>

790         800         810         820         830         840
               *           *           *           *           *           *
ATC ATT GGG GAC GAC ATC AAC CGA CGC TAT GAC TCA GAG TTC CAG ACC ATG TTG CAG CAC
TAG TAA CCC CTG CTG TAG TTG GCT GCG ATA CTG AGT CTC AAG GTC TGG TAC AAC GTC GTG
 I   I   G   D   D   I   N   R   R   Y   D   S   E   F   Q   T   M   L   Q   H>

>PstI
         |    850         860         870         880         890         900
         |     *           *           *           *           *           *
CTG CAG CCC ACG GCA GAG AAT GCC TAT GAG TAC TTC ACC AAG ATT GCC TCC AGC CTG TTT
GAC GTC GGG TGC CGT CTC TTA CGG ATA CTC ATG AAG TGG TTC TAA CGG AGG TCG GAC AAA
 L   Q   P   T   A   E   N   A   Y   E   Y   F   T   K   I   A   S   S   L   F>

910         920         930         940         950         960
               *           *           *           *           *           *
GAG AGT GGC ATC AAT TGG GGC CGT GTG GTG GCT CTT CTG GGC TTC AGC TAC CGT CTG GCC
CTC TCA CCG TAG TTA ACC CCG GCA CAC CAC CGA GAA GAC CCG AAG TCG ATG GCA GAC CGG
 E   S   G   I   N   W   G   R   V   V   A   L   L   G   F   S   Y   R   L   A>

970         980         990        1000        1010        1020
               *           *           *           *           *           *
CTA CAC ATC TAC CAG CGT GGC CTG ACT GGC TTC CTG GGC CAG GTG ACC CGC TTT GTG GTG
GAT GTG TAG ATG GTC GCA CCG GAC TGA CCG AAG GAC CCG GTC CAC TGG GCG AAA CAC CAC
 L   H   I   Y   Q   R   G   L   T   G   F   L   G   Q   V   T   R   F   V   V>

1030        1040        1050        1060        1070        1080
               *           *           *           *           *           *
GAC TTC ATG CTG CAT CAC TGC ATT GCC CGG TGG ATT GCA CAG AGG GGT GGC TGG GTG GCA
CTG AAG TAC GAC GTA GTG ACG TAA CGG GCC ACC TAA CGT GTC TCC CCA CCG ACC CAC CGT
 D   F   M   L   H   H   C   I   A   R   W   I   A   Q   R   G   G   W   V   A>

1090        1100        1110        1120        1130        1140
               *           *           *           *           *           *
GCC CTG AAC TTG GGC AAT GGT CCC ATC CTG AAC GTG CTG GTG GTT CTG GGT GTG GTT CTG
CGG GAC TTG AAC CCG TTA CCA GGG TAG GAC TTG CAC GAC CAC CAA GAC CCA CAC CAA GAC
 A   L   N   L   G   N   G   P   I   L   N   V   L   V   V   L   G   V   V   L>

1150        1160        1170        1180        1190        1200
               *           *           *           *           *           *
TTG GGC CAG TTT GTG GTA CGA AGA TTC TTC AAA TCA TGA CTC CCA AGG GTG CCT TTG GGG
AAC CCG GTC AAA CAC CAT GCT TCT AAG AAG TTT AGT ACT GAG GGT TCC CAC GGA AAC CCC
 L   G   Q   F   V   V   R   R   F   F   K   S   *>

1210        1220        1230        1240        1250        1260
               *           *           *           *           *           *
TCC CAG TTC AGA CCC CTG CCT GGA CTT AAG CGA AGT CTT TGC CTT CTC TGC TCC TTG CAG
AGG GTC AAG TCT GGG GAC GGA CCT GAA TTC GCT TCA GAA ACG GAA GAG ACG AGG AAC GTC

>Hind3
             1270        1280   |
               *           *   |
GGT CCC CCC TCA AGA GTA CAG AAG CTT
CCA GGG GGG AGT TCT CAT GTC TTC GAA
```

Figure 6

```
cdn1                                                           masgqgpgpprqecgepalpsaseeqvaqdteevfrsyvfyrhqqeqeaeqvaapadpemvt
cdn2                                                           masgqgpgpprqecgepalpsaseeqvaqdteevfrsyvfyHhqqeqeaeqAaapadpemvt
bcl2                                              mahagrtgyDNREIVMKYIHYKLSQRGYEWdagdvgaappgaapapgifssqpghtphtaasrdpvartsplqtpaapgaa
bax                                                                                                    mdgsgepprgggptsseqimktgalllqgfiqdragrmggeap
bcl-x                                              msqSNRELVDFLSYKLSQKGYSWsqfsdvseenrteapegteseemetpsalngnpswhladopavngatghasal
mcl-1                                  ...(+123 aa)eldgyepeplgkrpavlplelvgesGnntstdgslpstpppaeeeedelyrqelelisrylreqatgakdtk
A1                                                                                                         maeselmhlhslaehylqyvlq
bhrf
LMW5-HL                                                                                                           megeeliyhnllnellvgy
ced9                                  mtrctadnsltnpayrrrtmatgemkeflgikgteptdfginsdaqdlpspsrqastrrmslgesldgkindweeprlDIEGFVVDYFTHRIRQNGMEWfgapg cdn1     lplqpsstmgQVGRQLAIIGDDINRRYDSEFQTMLQHLQPTAENAYEYFTKIATSLFESGI-NWGRVVALLGFGYRLALHVYQHCLTGFLGQVTRFVVDFMLHH
cdn2     lplqpsstmgQVGRQLAIIGDDINRRYDSEFQTMLQHLQPTAENAYEYFTKIASSLFESGI-NWGRVVALLGFSYRLALHIYQRGLTGFLGQVTRFVVDFMLHH
bcl2     agpalspvppVVHLTLRQAGDDFSRRYRRDFAEMSRQLHLtpftargRFATVVEELFRDGV-NWGRIVAFFEFGGVMCVESVNREMSPLVDNIALWMTEY-LNR
bax      claldpvpqdastkklseclkrigdeldsnmelqrmisavdtdsprevFFRVAADMFSDGNFNWGRVVALFYFASKLVLKALCTKVPELIRTIMGWTLDF-LRE
bcl-x    darevipma-AVKQALREAGDEFELRYRRAFSDLTSQLHITPGTAYQSFEQVVNELFRDGV-NWGRIVAFFSFGGALCVESVDKEMQVLVSRIAAWMATY-LND
mcl-1    pmgrsgatsrkalETLRRVGDGVQRNHETVFQGMLRKLDIKNEDDVKSLSRVMIHVFSDGVTNWGRIVTLISFGAFVAKHLKTINQESCIEPLAESITD-VLVR
A1       vpafesapsqacrvlqrvafsvqkeveknlksylddfhvesldtarlifNQVMEKEFEDGIINWGRIVTIFAFGGVLLKKLpqeqlaldvcaykqvssfvaefl
bhrf     etplrlspedtvvlryhvlleeilernsetftetwnrflthtchvdldfnsvflelfhD-LINWGRICGFIVFSARMAKYCKDANn-HLESTVITTAYNF-SEG
LMW5-HL  lkyymndihelspyggqikklltyydeclnkqvtltfsltnaqelktQFTGVVTELFKrgdpslgralawmawcmhacrtlccnqstpyyvvdlsvrgmleaM-
ced9     lpcgvqpehemmrvmgtlfekkhaenfetfceqLlavprlsfslyqdvvrtvgnaqtdqcpMSYGRLIGLISFGGFVAAKmesvelqggvrnlfvytelfIKT cdn1     CIAR--WIA-QR-GGWVAALNLGngpllnvlvvlgvvllgqfvvrrffks                             SEQ ID NO.: 7
cdn2     CIAR--WIA-QR-GGWVAALNLGngpllnvlvvlgvvllgqfvvrrffks                             SEQ ID NO.: 9
bcl2     HLHT--WI--QDNGGWDAFVELYgpsmrplfdfswlslktllslalvgacltlgaylghk                   SEQ ID NO.: 12
bax      RLLG--WI--QDQGGWDGLLSYFgtgptwqtvtlfvagvltasltlwkkmg                            SEQ ID NO.: 13
bcl-x    HLEP--WI--QENGGWDTFVELYgnnaaaesrkgqerfnrwfltgmtvagvvllgolfork                  SEQ ID NO.: 14
mcl-1    TKRD--WLVKQ--RGWDGFVEFFhvedleggirnvllafagvagvgaglaylir                         SEQ ID NO.: 15
A1       MNNTGEWI-RQ-NGGWEDgflkkfepksgwltflqmtggiwemlfllk                               SEQ ID NO.: 16
bhrf     -LDG--WIHQQ--GGWstllednlpgsrrfswtiflagltlollvicsylfiorgrh                      SEQ ID NO.: 17
LMW5-HL  KHNLLPWMISH--GQQEEFLAFslhsqlysvlfnlkyflskfcnhhflrscvqllrkcnli                  SEQ ID NO.: 18
ced9     -RIRNNWKE-H-NRSWDDFMTLgkpmkedyeraeaekvgrrkqnrrwsmlgagvtagaigivgvvvcgrmmfslk    SEQ ID NO.: 19
```

SEQ ID NO.: 20

Figure 7A

```
                *         *         *         *         *         *         *         60
                                                                                       *
GAATTCTGGT AATTAGTTAA ACAACCTTGA ACAAGTTGTT TCACTTCTCT GAGTCTCAGT TTCTCACTCA AAAATGGTGA

*         *         *         *         *         *         *         160
                                                                                       *
ATAATTTGTA AGACTTCGCT AATAATCTAC GACTCTACAA GAGGCAATAG GGTACTGTGG ACAGAGAGCA GGCTTTGGAA

*         *         *         *         *         *         *         240
                                                                                       *
ACACACAAGA CTGGGTTTAG ATTCCTGCAC TCCACCCAGT GTGTGACTTG GCCAAGCTTC TTCACTTCTC TAAACCCCCA

*         *         *         *         *         *         *         320
                                                                                       *
TCTGTGTATC TGTACAGGAA TGAATGAATG AGTATGTGCA GCCAAGCTAT GCAAACTCCA GGTTAAAATA TTGCCTTGGG

*         *         *         *         *         *         *         400
                                                                                       *
TTTTTTAGTA AATTGTTCAA GCCCATGACA TTCTAGCAGA AAAAGCCTAG TGTCTCTTTC TTAAGGTGAT TGTGTCCATG

*         *         *         *         *         *         *         480
                                                                                       *
TGTTTTCCAG GAACTCTATG GGTTTCTCAA CCCAAATTCA CCCTGCCCTT GACCAAATGG CTCACCAGCT TCACGGATGC

*         *         *         *         *         *         *         560
                                                                                       *
TGCTCTGATG ACACACCCTG CAGTCAGCAT CTGCCCCTGC AGCTAGAATG GATTTCTGAG TGGGCATTAG CTGGGGATA

*         *         *         *         *         *         *         640
                                                                                       *
CCACATGGGC ACCAATGTCA CAGATCTTCT GTCACAGTCC ACCCCGAACC ATTGCTTCTC AAATCATAAT CCCTTAGCAG

*         *         *         *         *         *         *         720
                                                                                       *
GACAGCTAGG TGCAGCACGC ATGACACAAA CACCAGCCCT TGCCTACAAT CTCAGCCACT ATCTTGAGTC TGAGCAACTA

*         *         *         *         *         *         *         800
                                                                                       *
GTCTAGTGGC AGCCGCGCCC TTCCTTTTCA AGAGAGTTCT GGGATCAGAT CCTTTCACAA ACAGATCCCT CCCCACCCTG

*         *         *         *         *         *         *         880
                                                                                       *
CCTGTTGTCC AGGTCTGCAC ACTGAAAAGT AAGACAGCAT TTGCTAAGCC ATATTTCAAA AAGTTTGCTT ATACCTTCAT

*         *         *         *         *         *         *         960
                                                                                       *
CTCAGGACAA CAAGTGCCTG CTTAAGAGCC TTATGTTTGT GTAACTGGTA TTTTTTTTTC CCCTGACCTT CCAAGGCCTA

*         *         *         *         *         *         *         1040
                                                                                       *
GTCTACTTTC TCCCTCCCTA GCTGAACAAA AGTGAAGTTG AAATAATTTG AACTACCCCT TTTAGTGGGC AGCCCATTTG

*         *         *         *         *         *         *         1120
                                                                                       *
ATTTTTACCT TAGCCAGAGC CTTAATTTGT CCATGTGAGC ATAGCAGTAC CTTGCAGCAC CTGAGGCACA ATACATTGTT

*         *         *         *         *         *         *         1200
                                                                                       *
TAAAGAGTGA CAGTGCGTCC CATTCCAATA AGAACCACAC TCAGAGCAAA GGTTCCCTCT CCTGTGTGGA GAGTGACCCA

*         *         *         *         *         *         *         1280
                                                                                       *
TGGTAGAAAA TTTGCAGACT TCGTTACCTC TTCATCAGTT GAAAAATCTA TTTATTCATT TATGCATTTA ATTTTCCCTA

*         *         *         *         *         *         *         1360
                                                                                       *
TCTAAGCCAG GGATAGTCAA ACATTTTCTG TAAAGGGCCA AGTAGCATGA TAAATATGTT AGGCTCTGCA GGCCACTTAC

*         *         *         *         *         *         *         1440
                                                                                       *
AGTTTTGTCA TGTATTCTTT TTTTGCTCCC TGTTTGTATT ATTTTGTTTA CAATGCTTTA AAAATGTAAA AAAACAGATG

*         *         *         *         *         *         *         1520
                                                                                       *
ATCACTGGAG TCTCACGGGT CCCTCGGGCC ACACAGGGAC AAGCAAAGGC TACATCCAGA TACCAGAAAT GCACTGACGC

*         *         *         *         *         *         *         1600
                                                                                       *
CCGTTCCTGG AAGCTGGGCT CCCACTCAGC CCCTGGGAGC AGCAGCCTCC AGCCCCTTGG GACCTTCAAC TCCACCCTGC
```

Figure 7B

```
          *          *          *          *          *          *          *
TGACCCACGC GGGTTGAGCC AGCATCCCTG GAGGCTGACA CTGTCCTCCA CTGAGACCTG AAAA ATG GCA TCG GGG
                                                                      M   A   S   G>
1680
    *          *          *          *          *          *          *
CAA GGC CCA GGG CCT CCC AGG CAG GAG TGC GGA AAG CCT GCC CTG CCC TCT GCT TCT GAG GAG CAG
 Q   G   P   G   P   P   R   Q   E   C   G   K   P   A   L   P   S   A   S   E   E   Q>
              1760
    *          *          *          *          *          *          *
GTA GCC CAG GAC ATG GAG GGG TTT TCC GCA GCT ACG TTT TTT ACC ACC ATC AGC AGG AAC AGG AGG
 V   A   Q   D   M   E   G   F   S   A   A   T   F   F   T   T   I   S   R   N   R   R>
                             1840
    *          *          *          *          *          *          *
CTG AAG GGG CGG CCG CCC CTG CCG ACC CAG AGA TGG TCA CCT TGC CCC TCC AAC CTA GCA GCA CCA
 L   K   G   R   P   P   L   P   T   Q   R   W   S   P   C   P   S   N   L   A   A   P>
                                                     1920
    *          *          *          *          *          *          *
TGG GGC AGG TGG GAC GGC AGC TCG CCA TCA CCA GGA CGA CAT CAA CCG GCA CTA TGA CTTCGGAGT
 W   G   R   W   D   G   S   S   P   S   P   G   R   H   Q   P   A   L   *>
                                                              2000
          *          *          *          *          *          *          *
TCCAGACCAT GCTGCAGCAC CTGCAGCCCA CGGCAGAGAA CGCCTACGAG TACTTCACCA AGATCGCCTC CAGCCTGTTT
                                                                2080
          *          *          *          *          *          *          *
GAGAGTGGCA TCAACCGGGG CCGTGTGGTG GCTCTCCTGG GCTTCGGCTA CCGTCTGGTC CTACATGTCT ACCAGCACGG
                                                                2160
          *          *          *          *          *          *          *
CTTGACTGGC TTCCTGGGCC TGGTGACCCG CTTCGTGGTC TTCATGCTGC AACAAGGCAT CGCCCGGTGG ATCTCGCAGA
                                                                2240
          *          *          *          *          *          *          *
GGGGCGGCTG GGTGGCAGCC CTGGACTTGG GCAATAGTCC CATCCTGAAC GTGCTGGTGG TTGTGGGTGT GGTTCTGCTG
                                                                2320
          *          *          *          *          *          *          *
GGCCAGTTTG TGGTAAGAAG ATTCTTCAAA TCATGACTCC CAGGGGTGTC CTTTGGGGTC CCAGCTGTGA CCCCTGCCTG
                                                                2400
          *          *          *          *          *          *          *
GACTTAAGCC AAGTCTTTGC CTTCCCCACT CCCTTGCAGG GGTCACCCTT CAAAAGTACA GAAGCTCTAG CAAGTGTGCA
                                                                2480
          *          *          *          *          *          *          *
CCCCCGCTGC GGAGGGCCCC TGCGTGGGGG CCAGTCAGGC TGCGGAGGCA CCTCAACATT GCACGGTGCT AGTGGGCCCT
                                                                2560
          *          *          *          *          *          *          *
CTCTCTGGGC CCAGGGGCTG TGCCCTCCTC CCTTGGCTCT CTGGGACCTC CTTAGTCTTG TCTGCTAGGC GCTGCAGAGG
                                                                2640
          *          *          *          *          *          *          *
CTGATAACTT GGGGAAGCAA GAGACTGGGA GCCACTCCTC CCCAGTAAGT GTTTAACGGT TTTAGCTTTT TATAATACCC
                                                                2720
          *          *          *          *          *          *          *
TTGGGAGAGC CCATTCCCAC CATTCTACCC AAGGCCGGGA TGTCTGGGGT GTGGGGTTG GTGGGTCGTA ACCTACGTGC
                                                                2800
          *          *          *          *          *          *          *
CCCAGGATTC AGCTATTCTG GAAGATCAGA GCCTAAGAGC TAGGACTTGA TCCTGGTCCT GGCCGTCCCT AAGCATCATG
                                                                2880
          *          *          *          *          *          *          *
TGTCCCAGGA GCAGGACTGA CTGGGAGAGG GGACCAAGGT CCTACCCAGC TCTCCCCGTG CCCCCATTCC TCCTCCGGCC
                                                                2960
          *          *          *          *          *          *          *
ATACTGCCTT TGCAGTTGGA CTCTCAGGGA TTCTGGGCTT GGGGTGTGGG GCGGCGTGGA GTAACAGGCC AGAGCTGTCT
                                                                3040
          *          *          *          *          *          *          *
GAACTTATGT GTCAGAAGCC TCCAAGCCTG CCTCCCAAGG TCCTCTCAGC TCTCTCCCTT CCTCTCTCCT TATAGATACT
```

Figure 7C

```
                                                          3120
TGCTCCCAAC  CCATTCACTA  CAGGTGAAGG  CCCTCACCCA  TCCCTGGGGG  CCTTGGGTGA  GTGATGCGCT  AAGGCCCCTC
                                                          3200
CCCGCCCAGA  CTACAGGGCT  TGGTTTAGGG  CTTGGTTTGT  TATTTCAGGG  ATAAGGAGTA  GGGAGTTCAT  CTGGAAGGTT
                                                          3280
CTAAGTGGGA  GAAGGACTAT  CAACACCACA  GGAATCCCAG  AGGTGGGATC  CTCCCTCATG  GCTCTGGCAC  AGTGTAATCC
                                                          3360
AGGGGTGGAG  ATAGGGAACT  GTGAATACCT  GAACTCTGTC  CCCCGACCCT  CCATGCTCCT  CACCTTTCTG  GGTCTCTCCT
                                                          3440
CAGTGTGGGG  GTGAGAGTAC  CTTCTCTATC  GGGCACAGCC  TAGGGTGTTG  GGGGTGAAGG  GGGAGAAGTT  CTTGATTCAG
                                                          3520
CCAAATGCAG  GGAGGGGAGG  CAGAAGGAGC  CCACAGGCCA  CTCCCTATCC  TCTGAGTGTT  TGGAAATAAA  CTGTGCAATC
                                                          3600
CCATCAAAAA  AAAAAAGGAG  AAAAAAATGT  AAAAAACATT  CTTAGCTGTA  AGCTACTTAT  AGGGGATAA   AGACAGGACT
                                                          3680
GTTAATGGAC  ACAAACATAC  AGTTAGAGAG  AAGAAATAAG  TTCTGTCCAG  GCACGGTGGC  TCACACCTCT  AACTCCAGCA
                                                          3760
CTTTGGGAGA  CCAAAGTGGG  AAGATCATTT  GAGTCCAGGA  GTTCGAGACC  AGCCTGGACA  ACATAGCAAG  ATCTTATCTC
                                                          3840
TACAGAAAAT  TTAAAAAAAA  GAAAAAAACT  AGCCGCACAG  GTCTGCAGTC  CTAGCTACTC  GGGAGGCTAA  GGTGGGAGAA
                                                          3920
TCCTTGAACC  CAGGGATTTA  GTTTGAGGTT  GCAGTGAGCT  ATGATTGCAC  CACTGCACTC  CAGACTGGGT  GACTGAGTGA
                                                          4000
GACCCTGTCT  CAAATATAAA  GAAGGAACAA  GTTCTAGTTT  TCAATAGCGC  AATAGGGTGA  GTGCAGTTAG  CAACAACATA
                                                          4080
TTGTGTATTT  CAAAATAGCT  ACAAGAGAGG  ATATGAAGTG  TTCCCCCAAA  CAAGGAATGA  TAACGTTCGA  GGTGACAGAT
                                                          4160
ACCTTAAATA  CCCTGATTTG  ATCATTACAC  ATTCAATGTA  TGTATCAAAA  TATTACATGT  ACCCCACAAA  TTTGTGTAAA
                                                          4240
TATTATGTAT  CCACTTTTTA  AAGTTGGCAG  AGCCCAAAAG  CACTACTATG  GCTTCCAGTG  GTCACTGTGA  GCACTGCCAG
                                                          4320
CTCAGCAAAT  GTATCACCCA  AAATCTGGGC  AATGTGGGAA  ATTGGCTTCA  TGGCAGCTAT  GGCTTTGCCA  CTGATAGGAA
                                                          4400
TGATTTCCAG  AGATACTTAA  TCCTCAATTC  GGGACTCTTT  GCTTCAGGAG  TTTGGCTGGC  CAGGAACATG  AGTGACAGTG
                                                          4480
ACCTCTTGGC  ACTTCAGCTG  GGGGTGTAGC  CAAGCAGACA  AATGGAATCT  TGTGCTGAAC  CCAAACCTTC  TAGAAACAGA
                                                          4560
GCCTGTGAGC  ATCACAAGAT  ATGCCCTGAT  GGAAGCTGAA  GTTTAATTCA  GCTGAGCGCT  TGCCCCTTTC  CAACCTGGTT
                                                          4640
TCTTTTTGTT  CCTTGAGTCC  AGTCAGAATG  CCATTCCCTG  GCCAGCAGCC  AGCCTTTAGT  GACTGTCTCT  GTTCTGCAAA
```

Figure 7D

```
                                                              4720
GCTCTGTATA TAGTTACTGA GTTTCTGCAG GGGGTGATCT TTGCTCTTGT CCTAAGAAAT AACTACAGTG TTTTAAGAAA
                                                              4800
TATTTGAGGC CGGGTGCAGT GGTTCACACC TGTAATCCAG CACTTTGGGA GGCCAAGGCA GGTGGATCAT GAGGTCAAGA
                                                              4880
GTTTGAGACC ATCATGGCCA ACATGGTGAA ACCCCATCTC TACTAAAAAT ACAAAAATTA GCTGGGTGTG GTGGCGGGCA
                                                              4960
CCTGTAGTCC CAGCTACTCG GGAGGCTGAG GCAGGAGAAT CGCTTGAGCC TGGGAGGCGG AGGTTGCACT GAGCCGATAT
                                                              5040
CACGCCACTG CACTCCAGCC TGGCGACAGA GCGAGACTCC ATCTCAAAAA AAAGAAAAAA TAAATAGTTG AAATAAAGAC
                                                              5120
TGCACATAAA GACAAAAAAA AAGTTTATAA AGTTAAAAAA TAAAATAAAA AACAGGCTCC AGGCTGGATT GGGCCCAGAG
                                                              5200
GCTGTAGGAC ACAGACCCCC AGGCAATGAC TTCATAAATC CGGATGTTAA TCAGCCTCAC CTGGGAATTT GGGGAGGGGA
                                                              5280
CTCATTTTAA AACAGTTTCC TGGATTCTAA CCCAACCCAG AAAATCAGAC TCTTTGAGCT AAATTCTTAA GCTCCCTGGT
                                                              5360
GATGATGATG GAACCAGTTT ATGGCTGACC CCAGAGTACC GTCTGAAAGA CGTGCCACAT CCCTCTCTCT CCAGCCTCCC

CTTCTCCTCC ATTCCCCAGG GAGAATTC
```

Figure 11

SEQ ID NO.: 10

LPLQPSSTMGQVGRQLAIIGDDINRRYDSEFQTMLQHLQPTAENAYEYFTKIATSLFESGNWGRVVALLGFYRLALHVYQHGLTGFLGQVTRFVVDFMLHH
      →Δ2                           →Δ3
MASGQGPGPPRQECGEPALPSASEEQVAQDTEEVFRSYVFYRHQQEQEAEGVAAPADPEMVT ↑Δ1

CIARWIAQRGGWVAALNLGNGPILNVLVVLGVVLLGQFVVRRFFKS 5,770,443

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:

( A ) LENGTH: 8 amino acids
        ( B ) TYPE: amino acid
        ( C ) STRANDEDNESS: single ( D ) TOPOLOGY: linear ( x i ) SEQUENCE DESCRIPTION: SEQ ID NO:1:

Asp Trp Gly Arg Val Val Ala Ile
1               5

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i x ) FEATURE:
        ( A ) NAME/KEY: Modified Base
        ( B ) LOCATION: 23...23
        ( D ) OTHER INFORMATION: Inosine
        ( A ) NAME/KEY: Modified Base
        ( B ) LOCATION: 27...27
        ( D ) OTHER INFORMATION: Inosine ( x i ) SEQUENCE DESCRIPTION: SEQ ID NO:2:

AGATCTGAAT TCAACTTGGG GGNCAGNAGT NGTNGC    36

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Asp Trp Gly Gly Gln Glu Asn Asp Gln Ile Trp
1               5                   10

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( A ) NAME/KEY: Modified Base
        ( B ) LOCATION: 6...6
        ( D ) OTHER INFORMATION: Inosine
        ( A ) NAME/KEY: Modified Base
        ( B ) LOCATION: 9...9
        ( D ) OTHER INFORMATION: Inosine ( x i ) SEQUENCE DESCRIPTION: SEQ ID NO:4:

AGGGTNGGNG GNACNAGAGA CATCTAGGT    29

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i x ) FEATURE:
        ( A ) NAME/KEY: Modified Base
        ( B ) LOCATION: 19...19
        ( D ) OTHER INFORMATION: Inosine
        ( A ) NAME/KEY: Modified Base
        ( B ) LOCATION: 22...22
        ( D ) OTHER INFORMATION: Inosine ( x i ) SEQUENCE DESCRIPTION: SEQ ID NO:5:

AGATCTAAGC TTGTCCCANC CNCCNTGNTC CTTGAGATCC A    41

( 2 ) INFORMATION FOR SEQ ID NO:6:

( i ) SEQUENCE CHARACTERISTICS:
        ( A ) LENGTH: 2094 base pairs
        ( B ) TYPE: nucleic acid
        ( C ) STRANDEDNESS: double
        ( D ) TOPOLOGY: linear ( i x ) FEATURE:
        ( A ) NAME/KEY: Coding Sequence
        ( B ) LOCATION: 201...833
        ( D ) OTHER INFORMATION:

( x i ) SEQUENCE DESCRIPTION: SEQ ID NO:6:

```
GAGGATCTAC AGGGGACAAG TAAAGGCTAC ATCCAGATGC CGGGAATGCA CTGACGCCCA        60

TTCCTGGAAA CTGGGCTCCC ACTCAGCCCC TGGGAGCAGC AGCCGCCAGC CCCTCGGACC       120

TCCATCTCCA CCCTGCTGAG CCACCCGGGT TGGGCCAGGA TCCCGGCAGG CTGATCCCGT       180

CCTCCACTGA GACCTGAAAA ATG GCT TCG GGG CAA GGC CCA GGT CCT CCC           230
                      Met Ala Ser Gly Gln Gly Pro Gly Pro Pro
                        1               5                 10

AGG CAG GAG TGC GGA GAG CCT GCC CTG CCC TCT GCT TCT GAG GAG CAG         278
Arg Gln Glu Cys Gly Glu Pro Ala Leu Pro Ser Ala Ser Glu Glu Gln
             15              20              25

GTA GCC CAG GAC ACA GAG GAG GTT TTC CGC AGC TAC GTT TTT TAC CGC         326
Val Ala Gln Asp Thr Glu Glu Val Phe Arg Ser Tyr Val Phe Tyr Arg
                 30              35              40

CAT CAG CAG GAA CAG GAG GCT GAA GGG GTG GCT GCC CCT GCC GAC CCA         374
His Gln Gln Glu Gln Glu Ala Glu Gly Val Ala Ala Pro Ala Asp Pro
         45              50              55

GAG ATG GTC ACC TTA CCT CTG CAA CCT AGC AGC ACC ATG GGG CAG GTG         422
Glu Met Val Thr Leu Pro Leu Gln Pro Ser Ser Thr Met Gly Gln Val
 60              65              70

GGA CGG CAG CTC GCC ATC ATC GGG GAC GAC ATC AAC CGA CGC TAT GAC         470
Gly Arg Gln Leu Ala Ile Ile Gly Asp Asp Ile Asn Arg Arg Tyr Asp
 75              80              85              90

TCA GAG TTC CAG ACC ATG TTG CAG CAC CTG CAG CCC ACG GCA GAG AAT         518
Ser Glu Phe Gln Thr Met Leu Gln His Leu Gln Pro Thr Ala Glu Asn
             95              100             105

GCC TAT GAG TAC TTC ACC AAG ATT GCC ACC AGC CTG TTT GAG AGT GGC         566
Ala Tyr Glu Tyr Phe Thr Lys Ile Ala Thr Ser Leu Phe Glu Ser Gly
             110             115             120

ATC AAT TGG GGC CGT GTG GTG GCT CTT CTG GGC TTC GGC TAC CGT CTG         614
Ile Asn Trp Gly Arg Val Val Ala Leu Leu Gly Phe Gly Tyr Arg Leu
         125             130             135

GCC CTA CAC GTC TAC CAG CAT GGC CTG ACT GGC TTC CTA GGC CAG GTG         662
Ala Leu His Val Tyr Gln His Gly Leu Thr Gly Phe Leu Gly Gln Val
 140             145             150

ACC CGC TTC GTG GTC GAC TTC ATG CTG CAT CAC TGC ATT GCC CGG TGG         710
Thr Arg Phe Val Val Asp Phe Met Leu His His Cys Ile Ala Arg Trp
155             160             165             170

ATT GCA CAG AGG GGT GGC TGG GTG GCA GCC CTG AAC TTG GGC AAT GGT         758
Ile Ala Gln Arg Gly Gly Trp Val Ala Ala Leu Asn Leu Gly Asn Gly
             175             180             185

CCC ATC CTG AAC GTG CTG GTG GTT CTG GGT GTG GTT CTG TTG GGC CAG         806
Pro Ile Leu Asn Val Leu Val Val Leu Gly Val Val Leu Leu Gly Gln
             190             195             200

TTT GTG GTA CGA AGA TTC TTC AAA TCA TGACTCCCAA GGGTGCCCTT TGGGTCC       860
Phe Val Val Arg Arg Phe Phe Lys Ser
```

-continued

```
                205                 210
CGGTTCAGAC CCCTGCCTGG ACTTAAGCGA AGTCTTTGCC TTCTCTGTTC CCTTGCAGGG    920
TCCCCCCTCA AGAGTACAGA AGCTTTAGCA AGTGTGCACT CCAGCTTCGG AGGCCCTGCG    980
TGGGGGCCAG TCAGGCTGCA GAGGCACCTC AACATTGCAT GGTGCTAGTG CCCTCTCTCT   1040
GGGCCCAGGG CTGTGGCCGT CTCCTCCCTC AGCTCTCTGG GACCTCCTTA GCCCTGTCTG   1100
CTAGGCGCTG GGGAGACTGA TAACTTGGGG AGGCAAGAGA CTGGGAGCCA CTTCTCCCCA   1160
GAAAGTGTTT AACGGTTTTA GCTTTTTATA ATACCCTTGT GAGAGCCCAT TCCCACCATT   1220
CTACCTGAGG CCAGGACGTC TGGGGTGTGG GGATTGGTGG GTCATGTTC  CCCAGGATTC   1280
AGCTATTCTG GAAGATCAGC ACCCTAAGAG ATGGGACTAG GACCTGAGCC TGGTCCTGGC   1340
CGTCCCTAAG CATGTGTCCC AGGAGCAGGA CCTACTAGGA GAGGGGGCC  AAGGTCCTGC   1400
TCAACTCTAC CCCTGCTCCC ATTCCTCCCT CCGGCCATAC TGCCTTTGCA GTTGGACTCT   1460
CAGGGATTCT GGGCTTGGGG TGTGGGGTGG GGTGGAGTCG CAGACCAGAG CTGTCTGAAC   1520
TCACGTGTCA GAAGCCTCCA AGCCTGCCTC CCAAGGTCCT CTCAGTTCTC TCCCTTCCTC   1580
TCTCCTTATA GACACTTGCT CCCAACCCAT TCACTACAGG TGAAGGCTCT CACCCATCCC   1640
TGGGGGCCTT GGGTGAGTGG CCTGCTAAGG CTCCTCCTTG CCCAGACTAC AGGGCTTAGG   1700
ACTTGGTTTG TTATATCAGG GAAAAGGAGT AGGGAGTTCA TCTGGAGGGT TCTAAGTGGG   1760
AGAAGGACTA TCAACACCAC TAGGAATCCC AGAGGTGGAT CCTCCCTCAT GGCTCTGGCA   1820
CAGTGTAATC CAGGGGTGTA GATGGGGGAA CTGTGAATAC TTGAACTCTG TTCCCCCACC   1880
CTCCATGCTC CTCACCTGTC TAGGTCTCCT CAGGGTGGGG GGTGACAGTG CCTTCTCTAT   1940
TGGCACAGCC TAGGGTCTTG GGGGTCAGGG GGGAGAAGTT CTTGATTCAG CCAAATGCAG   2000
GGAGGGGAGG CAGATGGAGC CCATAGGCCA CCCCCTATCC TCTGAGTGTT TGGAAATAAA   2060
CTGTGCAATC CCCTCAAAAA AAAAACGGAG ATCC                               2094
```

( 2 ) INFORMATION FOR SEQ ID NO:7:

( i ) SEQUENCE CHARACTERISTICS:
        ( A ) LENGTH: 211 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:7:

```
Met Ala Ser Gly Gln Gly Pro Gly Pro Pro Arg Gln Glu Cys Gly Glu
 1               5                  10                  15

Pro Ala Leu Pro Ser Ala Ser Glu Glu Gln Val Ala Gln Asp Thr Glu
                20                  25                  30

Glu Val Phe Arg Ser Tyr Val Phe Tyr Arg His Gln Gln Glu Gln Glu
            35                  40                  45

Ala Glu Gly Val Ala Ala Pro Ala Asp Pro Glu Met Val Thr Leu Pro
        50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110
```

| | | | | | | | | | | | | | | |
|---|---|---|---|---|---|---|---|---|---|---|---|---|---|---|
| Lys | Ile | Ala<br>115 | Thr | Ser | Leu | Phe | Glu<br>120 | Ser | Gly | Ile | Asn | Trp<br>125 | Gly | Arg | Val |
| Val | Ala | Leu<br>130 | Leu | Gly | Phe | Gly<br>135 | Tyr | Arg | Leu | Ala | Leu<br>140 | His | Val | Tyr | Gln |
| His<br>145 | Gly | Leu | Thr | Gly | Phe<br>150 | Leu | Gly | Gln | Val | Thr<br>155 | Arg | Phe | Val | Val | Asp<br>160 |
| Phe | Met | Leu | His | His<br>165 | Cys | Ile | Ala | Arg | Trp<br>170 | Ile | Ala | Gln | Arg | Gly<br>175 | Gly |
| Trp | Val | Ala | Ala<br>180 | Leu | Asn | Leu | Gly | Asn<br>185 | Gly | Pro | Ile | Leu | Asn<br>190 | Val | Leu |
| Val | Val | Leu<br>195 | Gly | Val | Val | Leu | Leu<br>200 | Gly | Gln | Phe | Val | Val<br>205 | Arg | Arg | Phe |
| Phe | Lys | Ser<br>210 | | | | | | | | | | | | | |

(2) INFORMATION FOR SEQ ID NO:8:

( i ) SEQUENCE CHARACTERISTICS:
        ( A ) LENGTH: 1287 base pairs
        ( B ) TYPE: nucleic acid
        ( C ) STRANDEDNESS: double
        ( D ) TOPOLOGY: linear ( i x ) FEATURE:
        ( A ) NAME/KEY: Coding Sequence
        ( B ) LOCATION: 544...1176
        ( D ) OTHER INFORMATION:

( x i ) SEQUENCE DESCRIPTION: SEQ ID NO:8:

```
TTTAATATA  AATTAATGTG  CTCTATTTAT  AGAGACAATA  CATGAAATAT  ACTTAATAAA    60

AATTCAAATG  TTATAGAACT  GAAAAGATG   AAAAGTAAAA  ACAACCTATT  CCCCAGAGGT   120

AGCCACTGTC  CATAGTTTCT  ATTTTAGATT  CTTTCCTTTA  TACAAGATTA  TTATAGCTTC   180

TATTTTTTGG  TGTATGAACT  GTAGTCCTAG  AGGATTTAT   TAGTTATGAG  TTCTATAACT   240

AAGATCCATC  ATCTTAGTTG  CTAAGAACGT  AGATACTGAG  AACATCATTT  AAAAAAACAT   300

TTTTGGCTGG  CACCTCATGA  TCACTGGAGT  CTCGCGGGTC  CCTCAGGCTG  CACAGGGACA   360

AGTAAAGGCT  ACATCCAGAT  GCTGGGAATG  CACTGACGCC  CATTCCTGGA  AACTGGGCTC   420

CCACTCAGCC  CCTGGGAGCA  GCAGCCGCCA  GCCCCTCGGG  ACCTCCATCT  CCACCCTGCT   480

GAGCCACCCG  GGTTGGGCCA  GGATCCCGGC  AGGCTGATCC  CGTCCTCCAC  TGAGACCTGA   540
```

| | | | | | | | | | | | | | | | | |
|---|---|---|---|---|---|---|---|---|---|---|---|---|---|---|---|---|
| AAA | ATG<br>Met<br>1 | GCT<br>Ala | TCG<br>Ser | GGG<br>Gly | CAA<br>Gln<br>5 | GGC<br>Gly | CCA<br>Pro | GGT<br>Gly | CCT<br>Pro | CCC<br>Pro<br>10 | AGG<br>Arg | CAG<br>Gln | GAG<br>Glu | TGC<br>Cys | GGA<br>Gly<br>15 | 588 |
| GAG<br>Glu | CCT<br>Pro | GCC<br>Ala | CTG<br>Leu | CCC<br>Pro<br>20 | TCT<br>Ser | GCT<br>Ala | TCT<br>Ser | GAG<br>Glu | GAG<br>Glu<br>25 | CAG<br>Gln | GTA<br>Val | GCC<br>Ala | CAG<br>Gln | GAC<br>Asp<br>30 | ACA<br>Thr | 636 |
| GAG<br>Glu | GAG<br>Glu | GTT<br>Val | TTC<br>Phe<br>35 | CGC<br>Arg | AGC<br>Ser | TAC<br>Tyr | GTT<br>Val | TTT<br>Phe<br>40 | TAC<br>Tyr | CAC<br>His | CAT<br>His | CAG<br>Gln | CAG<br>Gln<br>45 | GAA<br>Glu | CAG<br>Gln | 684 |
| GAG<br>Glu | GCT<br>Ala | GAA<br>Glu<br>50 | GGG<br>Gly | GCG<br>Ala | GCT<br>Ala | GCC<br>Ala | CCT<br>Pro<br>55 | GCC<br>Ala | GAC<br>Asp | CCA<br>Pro | GAG<br>Glu | ATG<br>Met<br>60 | GTC<br>Val | ACC<br>Thr | TTA<br>Leu | 732 |
| CCT<br>Pro | CTG<br>Leu | CAA<br>Gln<br>65 | CCT<br>Pro | AGC<br>Ser | AGC<br>Ser | ACC<br>Thr | ATG<br>Met<br>70 | GGG<br>Gly | CAG<br>Gln | GTG<br>Val | GGA<br>Gly | CGG<br>Arg<br>75 | CAG<br>Gln | CTC<br>Leu | GCC<br>Ala | 780 |
| ATC<br>Ile<br>80 | ATT<br>Ile | GGG<br>Gly | GAC<br>Asp | GAC<br>Asp | ATC<br>Ile<br>85 | AAC<br>Asn | CGA<br>Arg | CGC<br>Arg | TAT<br>Tyr | GAC<br>Asp<br>90 | TCA<br>Ser | GAG<br>Glu | TTC<br>Phe | CAG<br>Gln | ACC<br>Thr<br>95 | 828 |
| ATG<br>Met | TTG<br>Leu | CAG<br>Gln | CAC<br>His | CTG<br>Leu | CAG<br>Gln | CCC<br>Pro | ACG<br>Thr | GCA<br>Ala | GAG<br>Glu | AAT<br>Asn | GCC<br>Ala | TAT<br>Tyr | GAG<br>Glu | TAC<br>Tyr | TTC<br>Phe | 876 |

```
Met  Leu  Gln  His  Leu  Gln  Pro  Thr  Ala  Glu  Asn  Ala  Tyr  Glu  Tyr  Phe
               100                      105                     110

ACC  AAG  ATT  GCC  TCC  AGC  CTG  TTT  GAG  AGT  GGC  ATC  AAT  TGG  GGC  CGT        924
Thr  Lys  Ile  Ala  Ser  Ser  Leu  Phe  Glu  Ser  Gly  Ile  Asn  Trp  Gly  Arg
               115                      120                     125

GTG  GTG  GCT  CTT  CTG  GGC  TTC  AGC  TAC  CGT  CTG  GCC  CTA  CAC  ATC  TAC        972
Val  Val  Ala  Leu  Leu  Gly  Phe  Ser  Tyr  Arg  Leu  Ala  Leu  His  Ile  Tyr
               130                      135                     140

CAG  CGT  GGC  CTG  ACT  GGC  TTC  CTG  GGC  CAG  GTG  ACC  CGC  TTT  GTG  GTG       1020
Gln  Arg  Gly  Leu  Thr  Gly  Phe  Leu  Gly  Gln  Val  Thr  Arg  Phe  Val  Val
     145                           150                     155

GAC  TTC  ATG  CTG  CAT  CAC  TGC  ATT  GCC  CGG  TGG  ATT  GCA  CAG  AGG  GGT       1068
Asp  Phe  Met  Leu  His  His  Cys  Ile  Ala  Arg  Trp  Ile  Ala  Gln  Arg  Gly
160                      165                      170                     175

GGC  TGG  GTG  GCA  GCC  CTG  AAC  TTG  GGC  AAT  GGT  CCC  ATC  CTG  AAC  GTG       1116
Gly  Trp  Val  Ala  Ala  Leu  Asn  Leu  Gly  Asn  Gly  Pro  Ile  Leu  Asn  Val
               180                      185                     190

CTG  GTG  GTT  CTG  GGT  GTG  GTT  CTG  TTG  GGC  CAG  TTT  GTG  GTA  CGA  AGA       1164
Leu  Val  Val  Leu  Gly  Val  Val  Leu  Leu  Gly  Gln  Phe  Val  Val  Arg  Arg
               195                      200                     205

TTC  TTC  AAA  TCA  TGACTCCCAA  GGGTGCCTTT  GGGGTCCCAG  TTCAGACCCC  TGCCT             1221
Phe  Phe  Lys  Ser
               210

GGACTTAAGC  GAAGTCTTTG  CCTTCTCTGC  TCCTTGCAGG  GTCCCCCCTC  AAGAGTACAG                1281

AAGCTT                                                                                1287
```

( 2 ) INFORMATION FOR SEQ ID NO:9:

( i ) SEQUENCE CHARACTERISTICS:
        ( A ) LENGTH: 211 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:9:

```
Met  Ala  Ser  Gly  Gln  Gly  Pro  Gly  Pro  Pro  Arg  Gln  Glu  Cys  Gly  Glu
 1             5                        10                      15

Pro  Ala  Leu  Pro  Ser  Ala  Ser  Glu  Glu  Gln  Val  Ala  Gln  Asp  Thr  Glu
               20                       25                      30

Glu  Val  Phe  Arg  Ser  Tyr  Val  Phe  Tyr  His  His  Gln  Gln  Glu  Gln  Glu
               35                       40                      45

Ala  Glu  Gly  Ala  Ala  Ala  Pro  Ala  Asp  Pro  Glu  Met  Val  Thr  Leu  Pro
     50                       55                      60

Leu  Gln  Pro  Ser  Ser  Thr  Met  Gly  Gln  Val  Gly  Arg  Gln  Leu  Ala  Ile
65                       70                      75                            80

Ile  Gly  Asp  Asp  Ile  Asn  Arg  Arg  Tyr  Asp  Ser  Glu  Phe  Gln  Thr  Met
                    85                       90                      95

Leu  Gln  His  Leu  Gln  Pro  Thr  Ala  Glu  Asn  Ala  Tyr  Glu  Tyr  Phe  Thr
               100                      105                     110

Lys  Ile  Ala  Ser  Ser  Leu  Phe  Glu  Ser  Gly  Ile  Asn  Trp  Gly  Arg  Val
               115                      120                     125

Val  Ala  Leu  Leu  Gly  Phe  Ser  Tyr  Arg  Leu  Ala  Leu  His  Ile  Tyr  Gln
     130                      135                     140

Arg  Gly  Leu  Thr  Gly  Phe  Leu  Gly  Gln  Val  Thr  Arg  Phe  Val  Val  Asp
145                      150                     155                           160
```

```
Phe  Met  Leu  His  His  Cys  Ile  Ala  Arg  Trp  Ile  Ala  Gln  Arg  Gly  Gly
               165                      170                      175

Trp  Val  Ala  Ala  Leu  Asn  Leu  Gly  Asn  Gly  Pro  Ile  Leu  Asn  Val  Leu
               180                      185                      190

Val  Val  Leu  Gly  Val  Val  Leu  Leu  Gly  Gln  Phe  Val  Val  Arg  Arg  Phe
               195                      200                      205

Phe  Lys  Ser
          210
```

(2) INFORMATION FOR SEQ ID NO:10:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:10:

```
Met  Ala  Ser  Gly  Gln  Gly  Pro  Gly  Pro  Pro  Arg  Gln  Glu  Cys  Gly  Glu
 1                   5                        10                       15

Pro  Ala  Leu  Pro  Ser  Ala  Ser  Glu  Glu  Gln  Val  Ala  Gln  Asp  Thr  Glu
               20                       25                       30

Glu  Val  Phe  Arg  Ser  Tyr  Val  Phe  Tyr  Arg  His  Gln  Gln  Glu  Gln  Glu
               35                       40                       45

Ala  Glu  Gly  Val  Ala  Ala  Pro  Ala  Asp  Pro  Glu  Met  Val  Thr  Leu  Pro
 50                       55                       60

Leu  Gln  Pro  Ser  Ser  Thr  Met  Gly  Gln  Val  Gly  Arg  Gln  Leu  Ala  Ile
 65                       70                       75                       80

Ile  Gly  Asp  Asp  Ile  Asn  Arg  Arg  Tyr  Asp  Ser  Glu  Phe  Gln  Thr  Met
               85                       90                       95

Leu  Gln  His  Leu  Gln  Pro  Thr  Ala  Glu  Asn  Ala  Tyr  Glu  Tyr  Phe  Thr
               100                      105                      110

Lys  Ile  Ala  Thr  Ser  Leu  Phe  Glu  Ser  Gly  Ile  Asn  Trp  Gly  Arg  Val
               115                      120                      125

Val  Ala  Leu  Leu  Gly  Phe  Gly  Tyr  Arg  Leu  Ala  Leu  His  Val  Tyr  Gln
          130                      135                      140

His  Gly  Leu  Thr  Gly  Phe  Leu  Gly  Gln  Val  Thr  Arg  Phe  Val  Val  Asp
145                      150                      155                      160

Phe  Met  Leu  His  His  Cys  Ile  Ala  Arg  Trp  Ile  Ala  Gln  Arg  Gly  Gly
               165                      170                      175

Trp  Val  Ala  Ala  Leu  Asn  Leu  Gly  Asn  Gly  Pro  Ile  Leu  Asn  Val  Leu
               180                      185                      190

Val  Val  Leu  Gly  Val  Val  Leu  Leu  Gly  Gln  Phe  Val  Val  Arg  Arg  Phe
               195                      200                      205

Phe  Lys  Ser
          210
```

(2) INFORMATION FOR SEQ ID NO:11:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:11:

```
Met  Ala  Ser  Gly  Gln  Gly  Pro  Gly  Pro  Pro  Arg  Gln  Glu  Cys  Gly  Glu
 1                   5                        10                       15

Pro  Ala  Leu  Pro  Ser  Ala  Ser  Glu  Glu  Gln  Val  Ala  Gln  Asp  Thr  Glu
```

|  |  |  | 20 |  |  |  | 25 |  |  |  | 30 |  |  |
|---|---|---|---|---|---|---|---|---|---|---|---|---|---|
| Glu | Val | Phe<br>35 | Arg | Ser | Tyr | Val | Phe<br>40 | Tyr | His | His | Gln<br>45 | Gln | Glu | Gln | Glu |
| Ala | Glu<br>50 | Gly | Ala | Ala | Ala<br>55 | Pro | Ala | Asp | Pro | Glu<br>60 | Met | Val | Thr | Leu | Pro |
| Leu<br>65 | Gln | Pro | Ser | Ser | Thr<br>70 | Met | Gly | Gln | Val | Gly<br>75 | Arg | Gln | Leu | Ala | Ile<br>80 |
| Ile | Gly | Asp | Asp | Ile<br>85 | Asn | Arg | Arg | Tyr | Asp<br>90 | Ser | Glu | Phe | Gln | Thr<br>95 | Met |
| Leu | Gln | His | Leu<br>100 | Gln | Pro | Thr | Ala | Glu<br>105 | Asn | Ala | Tyr | Glu | Tyr<br>110 | Phe | Thr |
| Lys | Ile | Ala<br>115 | Ser | Ser | Leu | Phe | Glu<br>120 | Ser | Gly | Ile | Asn | Trp<br>125 | Gly | Arg | Val |
| Val | Ala<br>130 | Leu | Leu | Gly | Phe | Ser<br>135 | Tyr | Arg | Leu | Ala | Leu<br>140 | His | Ile | Tyr | Gln |
| Arg<br>145 | Gly | Leu | Thr | Gly | Phe<br>150 | Leu | Gly | Gln | Val | Thr<br>155 | Arg | Phe | Val | Val | Asp<br>160 |
| Phe | Met | Leu | His | His<br>165 | Cys | Ile | Ala | Arg | Trp<br>170 | Ile | Ala | Gln | Arg | Gly<br>175 | Gly |
| Trp | Val | Ala | Ala<br>180 | Leu | Asn | Leu | Gly | Asn<br>185 | Gly | Pro | Ile | Leu | Asn<br>190 | Val | Leu |
| Val | Val | Leu<br>195 | Gly | Val | Val | Leu | Leu<br>200 | Gly | Gln | Phe | Val | Val<br>205 | Arg | Arg | Phe |
| Phe | Lys | Ser<br>210 |  |  |  |  |  |  |  |  |  |  |  |  |  |

( 2 ) INFORMATION FOR SEQ ID NO:12:

( i ) SEQUENCE CHARACTERISTICS:
        ( A ) LENGTH: 239 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

| Met<br>1 | Ala | His | Ala | Gly<br>5 | Arg | Thr | Gly | Tyr | Asp<br>10 | Asn | Arg | Glu | Ile | Val<br>15 | Met |
|---|---|---|---|---|---|---|---|---|---|---|---|---|---|---|---|
| Lys | Tyr | Ile | His<br>20 | Tyr | Lys | Leu | Ser | Gln<br>25 | Arg | Gly | Tyr | Glu | Trp<br>30 | Asp | Ala |
| Gly | Asp | Val<br>35 | Gly | Ala | Ala | Pro | Pro<br>40 | Gly | Ala | Ala | Pro | Ala<br>45 | Pro | Gly | Ile |
| Phe | Ser<br>50 | Ser | Gln | Pro | Gly | His<br>55 | Thr | Pro | His | Thr | Ala<br>60 | Ala | Ser | Arg | Asp |
| Pro<br>65 | Val | Ala | Arg | Thr | Ser<br>70 | Pro | Leu | Gln | Thr | Pro<br>75 | Ala | Ala | Pro | Gly | Ala<br>80 |
| Ala | Ala | Gly | Pro | Ala<br>85 | Leu | Ser | Pro | Val | Pro<br>90 | Pro | Val | Val | His | Leu<br>95 | Thr |
| Leu | Arg | Gln | Ala<br>100 | Gly | Asp | Asp | Phe | Ser<br>105 | Arg | Arg | Tyr | Arg | Arg<br>110 | Asp | Phe |
| Ala | Glu | Met<br>115 | Ser | Arg | Gln | Leu | His<br>120 | Leu | Thr | Pro | Phe | Thr<br>125 | Ala | Arg | Gly |
| Arg | Phe<br>130 | Ala | Thr | Val | Val | Glu<br>135 | Glu | Leu | Phe | Arg | Asp<br>140 | Gly | Val | Asn | Trp |
| Gly<br>145 | Arg | Ile | Val | Ala | Phe<br>150 | Phe | Glu | Phe | Gly | Gly<br>155 | Val | Met | Cys | Val | Glu<br>160 |
| Ser | Val | Asn | Arg | Glu | Met | Ser | Pro | Leu | Val | Asp | Asn | Ile | Ala | Leu | Trp |

165                             170                              175
Met  Thr  Glu  Tyr  Leu  Asn  Arg  His  Leu  His  Thr  Trp  Ile  Gln  Asp  Asn
               180                       185                       190

Gly  Gly  Trp  Asp  Ala  Phe  Val  Glu  Leu  Tyr  Gly  Pro  Ser  Met  Arg  Pro
          195                      200                 205

Leu  Phe  Asp  Phe  Ser  Trp  Leu  Ser  Leu  Lys  Thr  Leu  Leu  Ser  Leu  Ala
     210                      215                      220

Leu  Val  Gly  Ala  Cys  Ile  Thr  Leu  Gly  Ala  Tyr  Leu  Gly  His  Lys
225                      230                 235

( 2 ) INFORMATION FOR SEQ ID NO:13:

( i ) SEQUENCE CHARACTERISTICS:
            ( A ) LENGTH: 192 amino acids
            ( B ) TYPE: amino acid
            ( C ) STRANDEDNESS: single
            ( D ) TOPOLOGY: linear ( x i ) SEQUENCE DESCRIPTION: SEQ ID NO:13:

Met  Asp  Gly  Ser  Gly  Glu  Gln  Pro  Arg  Gly  Gly  Pro  Thr  Ser  Ser
 1                 5                      10                      15

Glu  Gln  Ile  Met  Lys  Thr  Gly  Ala  Leu  Leu  Leu  Gln  Gly  Phe  Ile  Gln
               20                       25                       30

Asp  Arg  Ala  Gly  Arg  Met  Gly  Gly  Glu  Ala  Pro  Glu  Leu  Ala  Leu  Asp
               35                       40                       45

Pro  Val  Pro  Gln  Asp  Ala  Ser  Thr  Lys  Lys  Leu  Ser  Glu  Cys  Leu  Lys
     50                       55                       60

Arg  Ile  Gly  Asp  Glu  Leu  Asp  Ser  Asn  Met  Glu  Leu  Gln  Arg  Met  Ile
65                       70                       75                       80

Ala  Ala  Val  Asp  Thr  Asp  Ser  Pro  Arg  Glu  Val  Phe  Phe  Arg  Val  Ala
                    85                       90                       95

Ala  Asp  Met  Phe  Ser  Asp  Gly  Asn  Phe  Asn  Trp  Gly  Arg  Val  Val  Ala
               100                      105                      110

Leu  Phe  Tyr  Phe  Ala  Ser  Lys  Leu  Val  Leu  Lys  Ala  Leu  Cys  Thr  Lys
          115                      120                      125

Val  Pro  Glu  Leu  Ile  Arg  Thr  Ile  Met  Gly  Trp  Thr  Leu  Asp  Phe  Leu
     130                      135                      140

Arg  Glu  Arg  Leu  Leu  Gly  Trp  Ile  Gln  Asp  Gln  Gly  Gly  Trp  Asp  Gly
145                      150                      155                      160

Leu  Leu  Ser  Tyr  Phe  Gly  Thr  Pro  Thr  Trp  Gln  Thr  Val  Thr  Ile  Phe
               165                      170                      175

Val  Ala  Gly  Val  Leu  Thr  Ala  Ser  Leu  Thr  Ile  Trp  Lys  Lys  Met  Gly
               180                      185                      190

( 2 ) INFORMATION FOR SEQ ID NO:14:

( i ) SEQUENCE CHARACTERISTICS:
            ( A ) LENGTH: 233 amino acids
            ( B ) TYPE: amino acid
            ( C ) STRANDEDNESS: single
            ( D ) TOPOLOGY: linear ( x i ) SEQUENCE DESCRIPTION: SEQ ID NO:14:

Met  Ser  Gln  Ser  Asn  Arg  Glu  Leu  Val  Val  Asp  Phe  Leu  Ser  Tyr  Lys
 1                 5                      10                      15

Leu  Ser  Gln  Lys  Gly  Tyr  Ser  Trp  Ser  Gln  Phe  Ser  Asp  Val  Glu  Glu
               20                       25                       30

Asn  Arg  Thr  Glu  Ala  Pro  Glu  Gly  Thr  Glu  Ser  Glu  Met  Glu  Thr  Pro
               35                       40                       45

Ser Ala Ile Asn Gly Asn Pro Ser Trp His Leu Ala Asp Ser Pro Ala
50              55                  60

Val Asn Gly Ala Thr Gly His Ser Ser Ser Leu Asp Ala Arg Glu Val
65              70                  75                  80

Ile Pro Met Ala Ala Val Lys Gln Ala Leu Arg Glu Ala Gly Asp Glu
            85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
            165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

( 2 ) INFORMATION FOR SEQ ID NO:15:

( i ) SEQUENCE CHARACTERISTICS:
       ( A ) LENGTH: 226 amino acids
       ( B ) TYPE: amino acid
       ( C ) STRANDEDNESS: single
       ( D ) TOPOLOGY: linear ( x i ) SEQUENCE DESCRIPTION: SEQ ID NO:15:

Glu Leu Asp Gly Tyr Glu Pro Glu Pro Leu Gly Lys Arg Pro Ala Val
1               5                   10                  15

Leu Pro Leu Leu Glu Leu Val Gly Glu Ser Gly Asn Asn Thr Ser Thr
            20                  25                  30

Asp Gly Ser Leu Pro Ser Thr Pro Pro Pro Ala Glu Glu Glu Glu Asp
        35                  40                  45

Glu Leu Tyr Arg Gln Ser Leu Glu Ile Ile Ser Arg Tyr Leu Arg Glu
    50                  55                  60

Gln Ala Thr Gly Ala Lys Asp Thr Lys Pro Met Gly Arg Ser Gly Ala
65              70                  75                  80

Thr Ser Arg Lys Ala Leu Glu Thr Leu Arg Arg Val Gly Asp Gly Val
            85                  90                  95

Gln Arg Asn His Glu Thr Val Phe Gln Gly Met Leu Arg Lys Leu Asp
            100                 105                 110

Ile Lys Asn Glu Asp Asp Val Lys Ser Leu Ser Arg Val Met Ile His
        115                 120                 125

Val Phe Ser Asp Gly Val Thr Asn Trp Gly Arg Ile Val Thr Leu Ile
    130                 135                 140

Ser Phe Gly Ala Phe Val Ala Lys His Leu Lys Thr Ile Asn Gln Glu
145                 150                 155                 160

Ser Cys Ile Glu Pro Leu Ala Glu Ser Ile Thr Asp Val Leu Val Arg
            165                 170                 175

```
Thr  Lys  Arg  Asp  Trp  Leu  Val  Lys  Gln  Arg  Gly  Trp  Asp  Gly  Phe  Val
          180                      185                      190

Glu  Phe  Phe  His  Val  Glu  Asp  Leu  Glu  Gly  Gly  Ile  Arg  Asn  Val  Leu
     195                      200                      205

Leu  Ala  Phe  Ala  Gly  Val  Ala  Gly  Val  Gly  Ala  Gly  Leu  Ala  Tyr  Leu
210                      215                      220

Ile  Arg
225
```

(2) INFORMATION FOR SEQ ID NO:16:

(i) SEQUENCE CHARACTERISTICS:
        (A) LENGTH: 172 amino acids
        (B) TYPE: amino acid
        (C) STRANDEDNESS: single
        (D) TOPOLOGY: linear (xi) SEQUENCE DESCRIPTION: SEQ ID NO:16:

```
Met  Ala  Glu  Ser  Glu  Leu  Met  His  Ile  His  Ser  Leu  Ala  Glu  His  Tyr
1                        5                        10                       15

Leu  Gln  Tyr  Val  Leu  Gln  Val  Pro  Ala  Phe  Glu  Ser  Ala  Pro  Ser  Gln
               20                       25                       30

Ala  Cys  Arg  Val  Leu  Gln  Arg  Val  Ala  Phe  Ser  Val  Gln  Lys  Glu  Val
          35                       40                       45

Glu  Lys  Asn  Leu  Lys  Ser  Tyr  Leu  Asp  Asp  Phe  His  Val  Glu  Ser  Ile
     50                       55                       60

Asp  Thr  Ala  Arg  Ile  Ile  Phe  Asn  Gln  Val  Met  Glu  Lys  Glu  Phe  Glu
65                       70                       75                       80

Asp  Gly  Ile  Ile  Asn  Trp  Gly  Arg  Ile  Val  Thr  Ile  Phe  Ala  Phe  Gly
                    85                       90                       95

Gly  Val  Leu  Leu  Lys  Lys  Leu  Pro  Gln  Glu  Gln  Ile  Ala  Leu  Asp  Val
               100                      105                      110

Cys  Ala  Tyr  Lys  Gln  Val  Ser  Ser  Phe  Val  Ala  Glu  Phe  Ile  Met  Asn
          115                      120                      125

Asn  Thr  Gly  Glu  Trp  Ile  Arg  Gln  Asn  Gly  Gly  Trp  Glu  Asp  Gly  Phe
     130                      135                      140

Ile  Lys  Lys  Phe  Glu  Pro  Lys  Ser  Gly  Trp  Leu  Thr  Phe  Leu  Gln  Met
145                      150                      155                      160

Thr  Gly  Gln  Ile  Trp  Glu  Met  Leu  Phe  Leu  Leu  Lys
                    165                      170
```

(2) INFORMATION FOR SEQ ID NO:17:

(i) SEQUENCE CHARACTERISTICS:
        (A) LENGTH: 187 amino acids
        (B) TYPE: amino acid
        (C) STRANDEDNESS: single
        (D) TOPOLOGY: linear (xi) SEQUENCE DESCRIPTION: SEQ ID NO:17:

```
Met  Ala  Tyr  Ser  Thr  Arg  Glu  Ile  Leu  Leu  Ala  Leu  Cys  Ile  Arg  Asp
1                        5                        10                       15

Ser  Arg  Val  His  Gly  Asn  Gly  Thr  Leu  His  Pro  Val  Leu  Glu  Leu  Ala
               20                       25                       30

Ala  Arg  Glu  Thr  Pro  Leu  Arg  Leu  Ser  Pro  Glu  Asp  Thr  Val  Val  Leu
          35                       40                       45

Arg  Tyr  His  Val  Leu  Leu  Glu  Glu  Ile  Ile  Glu  Arg  Asn  Ser  Glu  Thr
     50                       55                       60
```

| Phe | Thr | Glu | Thr | Trp | Asn | Arg | Phe | Ile | Thr | His | Thr | Glu | His | Val | Asp |
| 65 | | | | | 70 | | | | | 75 | | | | | 80 |

| Leu | Asp | Phe | Asn | Ser | Val | Phe | Leu | Glu | Ile | Phe | His | Asp | Leu | Ile | Asn |
| | | | | 85 | | | | | 90 | | | | | 95 | |

| Trp | Gly | Arg | Ile | Cys | Gly | Phe | Ile | Val | Phe | Ser | Ala | Arg | Met | Ala | Lys |
| | | | 100 | | | | | 105 | | | | | 110 | | |

| Tyr | Cys | Lys | Asp | Ala | Asn | Asn | His | Leu | Glu | Ser | Thr | Val | Ile | Thr | Thr |
| | | 115 | | | | | 120 | | | | | 125 | | | |

| Ala | Tyr | Asn | Phe | Ser | Glu | Gly | Leu | Asp | Gly | Trp | Ile | His | Gln | Gln | Gly |
| | 130 | | | | | 135 | | | | | 140 | | | | |

| Gly | Trp | Ser | Thr | Leu | Ile | Glu | Asp | Asn | Ile | Pro | Gly | Ser | Arg | Arg | Phe |
| 145 | | | | | 150 | | | | | 155 | | | | | 160 |

| Ser | Trp | Thr | Leu | Phe | Leu | Ala | Gly | Leu | Thr | Leu | Ser | Leu | Leu | Val | Ile |
| | | | | 165 | | | | | 170 | | | | | 175 | |

| Cys | Ser | Tyr | Leu | Phe | Ile | Ser | Arg | Gly | Arg | His |
| | | | 180 | | | | | 185 | | |

( 2 ) INFORMATION FOR SEQ ID NO:18:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

| Met | Glu | Gly | Glu | Glu | Leu | Ile | Tyr | His | Asn | Ile | Ile | Asn | Glu | Ile | Leu |
| 1 | | | | 5 | | | | | 10 | | | | | 15 | |

| Val | Gly | Tyr | Ile | Lys | Tyr | Tyr | Met | Asn | Asp | Ile | His | Glu | Leu | Ser | Pro |
| | | | 20 | | | | | 25 | | | | | 30 | | |

| Tyr | Gln | Gln | Gln | Ile | Lys | Lys | Ile | Leu | Thr | Tyr | Tyr | Asp | Glu | Cys | Leu |
| | | | 35 | | | | | 40 | | | | | 45 | | |

| Asn | Lys | Gln | Val | Thr | Ile | Thr | Phe | Ser | Leu | Thr | Asn | Ala | Gln | Glu | Ile |
| | 50 | | | | | 55 | | | | | 60 | | | | |

| Lys | Thr | Gln | Phe | Thr | Gly | Val | Val | Thr | Glu | Leu | Phe | Lys | Arg | Gly | Asp |
| 65 | | | | | 70 | | | | | 75 | | | | | 80 |

| Pro | Ser | Leu | Gly | Arg | Ala | Leu | Ala | Trp | Met | Ala | Trp | Cys | Met | His | Ala |
| | | | | 85 | | | | | 90 | | | | | 95 | |

| Cys | Arg | Thr | Leu | Cys | Cys | Asn | Gln | Ser | Thr | Pro | Tyr | Tyr | Val | Val | Asp |
| | | | 100 | | | | | 105 | | | | | 110 | | |

| Leu | Ser | Val | Arg | Gly | Met | Leu | Glu | Ala | Met | Lys | His | Asn | Leu | Leu | Pro |
| | | | 115 | | | | | 120 | | | | | 125 | | |

| Trp | Met | Ile | Ser | His | Gly | Gly | Gln | Glu | Glu | Phe | Leu | Ala | Phe | Ser | Leu |
| | 130 | | | | | 135 | | | | | 140 | | | | |

| His | Ser | Gln | Ile | Tyr | Ser | Val | Ile | Phe | Asn | Ile | Lys | Tyr | Phe | Leu | Ser |
| 145 | | | | | 150 | | | | | 155 | | | | | 160 |

| Lys | Phe | Cys | Asn | His | His | Phe | Leu | Arg | Ser | Cys | Val | Gln | Leu | Leu | Arg |
| | | | | 165 | | | | | 170 | | | | | 175 | |

| Lys | Cys | Asn | Leu | Ile |
| | | | 180 | |

( 2 ) INFORMATION FOR SEQ ID NO:19:

( i ) SEQUENCE CHARACTERISTICS:
        ( A ) LENGTH: 280 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

| Met | Thr | Arg | Cys | Thr | Ala | Asp | Asn | Ser | Leu | Thr | Asn | Pro | Ala | Tyr | Arg |
| 1 | | | | 5 | | | | | 10 | | | | | 15 | |

| Arg | Arg | Thr | Met | Ala | Thr | Gly | Glu | Met | Lys | Glu | Phe | Leu | Gly | Ile | Lys |
| | | | 20 | | | | | 25 | | | | | 30 | | |

| Gly | Thr | Glu | Pro | Thr | Asp | Phe | Gly | Ile | Asn | Ser | Asp | Ala | Gln | Asp | Leu |
| | | 35 | | | | | 40 | | | | | 45 | | | |

| Pro | Ser | Pro | Ser | Arg | Gln | Ala | Ser | Thr | Arg | Arg | Met | Ser | Ile | Gly | Glu |
| | 50 | | | | | 55 | | | | | 60 | | | | |

| Ser | Ile | Asp | Gly | Lys | Ile | Asn | Asp | Trp | Glu | Glu | Pro | Arg | Leu | Asp | Ile |
| 65 | | | | | 70 | | | | 75 | | | | | 80 | |

| Glu | Gly | Phe | Val | Val | Asp | Tyr | Phe | Thr | His | Arg | Ile | Arg | Gln | Asn | Gly |
| | | | | 85 | | | | 90 | | | | | 95 | | |

| Met | Glu | Trp | Phe | Gly | Ala | Pro | Gly | Leu | Pro | Cys | Gly | Val | Gln | Pro | Glu |
| | | | 100 | | | | | 105 | | | | | 110 | | |

| His | Glu | Met | Met | Arg | Val | Met | Gly | Thr | Ile | Phe | Glu | Lys | Lys | His | Ala |
| | | 115 | | | | | 120 | | | | | 125 | | | |

| Glu | Asn | Phe | Glu | Thr | Phe | Cys | Glu | Gln | Leu | Leu | Ala | Val | Pro | Arg | Ile |
| | 130 | | | | | 135 | | | | | 140 | | | | |

| Ser | Phe | Ser | Leu | Tyr | Gln | Asp | Val | Val | Arg | Thr | Val | Gly | Asn | Ala | Gln |
| 145 | | | | | 150 | | | | | 155 | | | | | 160 |

| Thr | Asp | Gln | Cys | Pro | Met | Ser | Tyr | Gly | Arg | Leu | Ile | Gly | Leu | Ile | Ser |
| | | | | 165 | | | | | 170 | | | | | 175 | |

| Phe | Gly | Gly | Phe | Val | Ala | Ala | Lys | Met | Met | Glu | Ser | Val | Glu | Leu | Gln |
| | | | 180 | | | | | 185 | | | | | 190 | | |

| Gly | Gln | Val | Arg | Asn | Leu | Phe | Val | Tyr | Thr | Ser | Leu | Phe | Ile | Lys | Thr |
| | | 195 | | | | | 200 | | | | | 205 | | | |

| Arg | Ile | Arg | Asn | Asn | Trp | Lys | Glu | His | Asn | Arg | Ser | Trp | Asp | Asp | Phe |
| | 210 | | | | | 215 | | | | | 220 | | | | |

| Met | Thr | Leu | Gly | Lys | Gln | Met | Lys | Glu | Asp | Tyr | Glu | Arg | Ala | Glu | Ala |
| 225 | | | | | 230 | | | | | 235 | | | | | 240 |

| Glu | Lys | Val | Gly | Arg | Arg | Lys | Gln | Asn | Arg | Arg | Trp | Ser | Met | Ile | Gly |
| | | | | 245 | | | | | 250 | | | | | 255 | |

| Ala | Gly | Val | Thr | Ala | Gly | Ala | Ile | Gly | Ile | Val | Gly | Val | Val | Val | Cys |
| | | | 260 | | | | | 265 | | | | | 270 | | |

| Gly | Arg | Met | Met | Phe | Ser | Leu | Lys |
| | | 275 | | | | | 280 |

( 2 ) INFORMATION FOR SEQ ID NO:20:

( i ) SEQUENCE CHARACTERISTICS:
        ( A ) LENGTH: 5408 base pairs
        ( B ) TYPE: nucleic acid
        ( C ) STRANDEDNESS: double
        ( D ) TOPOLOGY: linear ( i x ) FEATURE:
        ( A ) NAME/KEY: Coding Sequence
        ( B ) LOCATION: 1665...1928
        ( D ) OTHER INFORMATION:

( x i ) SEQUENCE DESCRIPTION: SEQ ID NO:20:

```
GAATTCTGGT AATTAGTTAA CAACCTTGA  ACAAGTTGTT TCACTTCTCT GAGTCTCAGT      60

TTCTCACTCA AAAATGGTGA ATAATTTGTA AGACTTCGCT AATAATCTAC GACTCTACAA     120

GAGGCAATAG GGTACTGTGG ACAGAGAGCA GGCTTTGGAA ACACACAAGA CTGGGTTTAG     180

ATTCCTGCAC TCCACCCAGT GTGTGACTTG GCCAAGCTTC TTCACTTCTC TAAACCCCCA     240
```

-continued

```
TCTGTGTATC  TGTACAGGAA  TGAATGAATG  AGTATGTGCA  GCCAAGCTAT  GCAAACTCCA    300

GGTTAAAATA  TTGCCTTGGG  TTTTTTAGTA  AATTGTTCAA  GCCCATGACA  TTCTAGCAGA    360

AAAAGCCTAG  TGTCTCTTTC  TTAAGGTGAT  TGTGTCCATG  TGTTTTCCAG  GAACTCTATG    420

GGTTTCTCAA  CCCAAATTCA  CCCTGCCCTT  GACCAAATGG  CTCACCAGCT  TCACGGATGC    480

TGCTCTGATG  ACACACCCTG  CAGTCAGCAT  CTGCCCCTGC  AGCTAGAATG  GATTTCTGAG    540

TGGGCATTAG  CTGGGGGATA  CCACATGGGC  ACCAATGTCA  CAGATCTTCT  GTCACAGTCC    600

ACCCCGAACC  ATTGCTTCTC  AAATCATAAT  CCCTTAGCAG  GACAGCTAGG  TGCAGCACGC    660

ATGACACAAA  CACCAGCCCT  TGCCTACAAT  CTCAGCCACT  ATCTTGAGTC  TGAGCAACTA    720

GTCTAGTGGC  AGCCGCGCCC  TTCCTTTTCA  AGAGAGTTCT  GGGATCAGAT  CCTTTCACAA    780

ACAGATCCCT  CCCCACCCTG  CCTGTTGTCC  AGGTCTGCAC  ACTGAAAAGT  AAGACAGCAT    840

TTGCTAAGCC  ATATTTCAAA  AAGTTTGCTT  ATACCTTCAT  CTCAGGACAA  CAAGTGCCTG    900

CTTAAGAGCC  TTATGTTTGT  GTAACTGGTA  TTTTTTTTC   CCCTGACCTT  CCAAGGCCTA    960

GTCTACTTTC  TCCCTCCCTA  GCTGAACAAA  AGTGAAGTTG  AAATAATTTG  AACTACCCCT   1020

TTTAGTGGGC  AGCCCATTTG  ATTTTTACCT  TAGCCAGAGC  CTTAATTTGT  CCATGTGAGC   1080

ATAGCAGTAC  CTTGCAGCAC  CTGAGGCACA  ATACATTGTT  TAAAGAGTGA  CAGTGCGTCC   1140

CATTCCAATA  AGAACCACAC  TCAGAGCAAA  GGTTCCTCT   CCTGTGTGGA  GAGTGACCCA   1200

TGGTAGAAAA  TTTGCAGACT  TCGTTACCTC  TTCATCAGTT  GAAAAATCTA  TTTATTCATT   1260

TATGCATTTA  ATTTTCCCTA  TCTAAGCCAG  GGATAGTCAA  ACATTTTCTG  TAAAGGGCCA   1320

AGTAGCATGA  TAAATATGTT  AGGCTCTGCA  GGCCACTTAC  AGTTTTGTCA  TGTATTCTTT   1380

TTTTGCTCCC  TGTTTGTATT  ATTTTGTTTA  CAATGCTTTA  AAAATGTAAA  AAACAGATG    1440

ATCACTGGAG  TCTCACGGGT  CCCTCGGGCC  ACACAGGGAC  AAGCAAAGGC  TACATCCAGA   1500

TACCAGAAAT  GCACTGACGC  CCGTTCCTGG  AAGCTGGGCT  CCCACTCAGC  CCCTGGGAGC   1560

AGCAGCCTCC  AGCCCCTTGG  GACCTTCAAC  TCCACCCTGC  TGACCCACGC  GGGTTGAGCC   1620

AGCATCCCTG  GAGGCTGACA  CTGTCCTCCA  CTGAGACCTG  AAAA ATG GCA TCG GGG     1676
                                                 Met Ala Ser Gly
                                                   1
```

```
CAA GGC CCA GGG CCT CCC AGG CAG GAG TGC GGA AAG CCT GCC CTG CCC          1724
Gln Gly Pro Gly Pro Pro Arg Gln Glu Cys Gly Lys Pro Ala Leu Pro
  5           10                  15                  20

TCT GCT TCT GAG GAG CAG GTA GCC CAG GAC ATG GAG GGG TTT TCC GCA          1772
Ser Ala Ser Glu Glu Gln Val Ala Gln Asp Met Glu Gly Phe Ser Ala
              25                  30                  35

GCT ACG TTT TTT ACC ACC ATC AGC AGG AAC AGG AGG CTG AAG GGG CGG          1820
Ala Thr Phe Phe Thr Thr Ile Ser Arg Asn Arg Arg Leu Lys Gly Arg
          40                  45                  50

CCG CCC CTG CCG ACC CAG AGA TGG TCA CCT TGC CCC TCC AAC CTA GCA          1868
Pro Pro Leu Pro Thr Gln Arg Trp Ser Pro Cys Pro Ser Asn Leu Ala
      55                  60                  65

GCA CCA TGG GGC AGG TGG GAC GGC AGC TCG CCA TCA CCA GGA CGA CAT          1916
Ala Pro Trp Gly Arg Trp Asp Gly Ser Ser Pro Ser Pro Gly Arg His
  70                  75                  80

CAA CCG GCA CTA TGACTTCGGA GTTCCAGACC ATGCTGCAGC ACCTGCAGCC CACGG        1973
Gln Pro Ala Leu
 85

CAGAGAACGC CTACGAGTAC TTCACCAAGA TCGCCTCCAG CCTGTTTGAG AGTGGCATCA        2033

ACCGGGGCCG TGTGGTGGCT CTCCTGGGCT TCGGCTACCG TCTGGTCCTA CATGTCTACC        2093

AGCACGGCTT GACTGGCTTC CTGGGCCTGG TGACCCGCTT CGTGGTCTTC ATGCTGCAAC        2153
```

```
AAGGCATCGC CCGGTGGATC TCGCAGAGGG GCGGCTGGGT GGCAGCCCTG GACTTGGGCA    2213
ATAGTCCCAT CCTGAACGTG CTGGTGGTTG TGGGTGTGGT TCTGCTGGGC CAGTTTGTGG    2273
TAAGAAGATT CTTCAAATCA TGACTCCCAG GGGTGTCCTT TGGGGTCCCA GCTGTGACCC    2333
CTGCCTGGAC TTAAGCCAAG TCTTTGCCTT CCCCACTCCC TTGCAGGGGT CACCCTTCAA    2393
AAGTACAGAA GCTCTAGCAA GTGTGCACCC CCGCTGCGGA GGGCCCCTGC GTGGGGGCCA    2453
GTCAGGCTGC GGAGGCACCT CAACATTGCA CGGTGCTAGT GGGCCCTCTC TCTGGGCCCA    2513
GGGGCTGTGC CCTCCTCCCT TGGCTCTCTG GGACCTCCTT AGTCTTGTCT GCTAGGCGCT    2573
GCAGAGGCTG ATAACTTGGG GAAGCAAGAG ACTGGGAGCC ACTCCTCCCC AGTAAGTGTT    2633
TAACGGTTTT AGCTTTTTAT AATACCCTTG GGAGAGCCCA TTCCCACCAT TCTACCCAAG    2693
GCCGGGATGT CTGGGGTGTG GGGGTTGGTG GGTCGTAACC TACGTGCCCC AGGATTCAGC    2753
TATTCTGGAA GATCAGAGCC TAAGAGCTAG GACTTGATCC TGGTCCTGGC CGTCCCTAAG    2813
CATCATGTGT CCCAGGAGCA GGACTGACTG GGAGAGGGGA CCAAGGTCCT ACCCAGCTCT    2873
CCCCGTGCCC CCATTCCTCC TCCGGCCATA CTGCCTTTGC AGTTGGACTC TCAGGGATTC    2933
TGGGCTTGGG GTGTGGGGCG GCGTGGAGTA ACAGGCCAGA GCTGTCTGAA CTTATGTGTC    2993
AGAAGCCTCC AAGCCTGCCT CCCAAGGTCC TCTCAGCTCT CTCCCTTCCT CTCTCCTTAT    3053
AGATACTTGC TCCCAACCCA TTCACTACAG GTGAAGGCCC TCACCCATCC CTGGGGGCCT    3113
TGGGTGAGTG ATGCGCTAAG GCCCCTCCCC GCCCAGACTA CAGGGCTTGG TTTAGGGCTT    3173
GGTTTGTTAT TTCAGGGATA AGGAGTAGGG AGTTCATCTG GAAGGTTCTA AGTGGGAGAA    3233
GGACTATCAA CACCACAGGA ATCCCAGAGG TGGGATCCTC CCTCATGGCT CTGGCACAGT    3293
GTAATCCAGG GGTGGAGATA GGGAACTGTG AATACCTGAA CTCTGTCCCC CGACCCTCCA    3353
TGCTCCTCAC CTTTCTGGGT CTCTCCTCAG TGTGGGGGTG AGAGTACCTT CTCTATCGGG    3413
CACAGCCTAG GGTGTTGGGG GTGAAGGGGG AGAAGTTCTT GATTCAGCCA AATGCAGGGA    3473
GGGGAGGCAG AAGGAGCCCA CAGGCCACTC CCTATCCTCT GAGTGTTTGG AAATAAACTG    3533
TGCAATCCCA TCAAAAAAAA AAAGGAGAAA AAAATGTAAA AACATTCTT AGCTGTAAGC     3593
TACTTATAGG GGGATAAAGA CAGGACTGTT AATGGACACA AACATACAGT TAGAGAGAAG    3653
AAATAAGTTC TGTCCAGGCA CGGTGGCTCA CACCTCTAAC TCCAGCACTT GGGAGACCA    3713
AAGTGGGAAG ATCATTTGAG TCCAGGAGTT CGAGACCAGC CTGGACAACA TAGCAAGATC    3773
TTATCTCTAC AGAAAATTTA AAAAAAGAA AAAAACTAGC CGCACAGGTC TGCAGTCCTA     3833
GCTACTCGGG AGGCTAAGGT GGGAGAATCC TTGAACCCAG GGATTTAGTT TGAGGTTGCA    3893
GTGAGCTATG ATTGCACCAC TGCACTCCAG ACTGGGTGAC TGAGTGAGAC CCTGTCTCAA    3953
ATATAAAGAA GGAACAAGTT CTAGTTTTCA ATAGCGCAAT AGGGTGAGTG CAGTTAGCAA    4013
CAACATATTG TGTATTTCAA AATAGCTACA AGAGAGGATA TGAAGTGTTC CCCCAAACAA    4073
GGAATGATAA CGTTCGAGGT GACAGATACC TTAAATACCC TGATTGATC ATTACACATT     4133
CAATGTATGT ATCAAAATAT TACATGTACC CCACAAATTT GTGTAAATAT TATGTATCCA    4193
CTTTTTAAAG TTGGCAGAGC CCAAAAGCAC TACTATGGCT TCCAGTGGTC ACTGTGAGCA    4253
CTGCCAGCTC AGCAAATGTA TCACCCAAAA TCTGGGCAAT GTGGGAAATT GGCTTCATGG    4313
CAGCTATGGC TTTGCCACTG ATAGGAATGA TTTCCAGAGA TACTTAATCC TCAATTCGGG    4373
ACTCTTTGCT TCAGGAGTTT GGCTGGCCAG GAACATGAGT GACAGTGACC TCTTGGCACT    4433
TCAGCTGGGG GTGTAGCCAA GCAGACAAAT GGAATCTTGT GCTGAACCCA AACCTTCTAG    4493
AAACAGAGCC TGTGAGCATC ACAAGATATG CCCTGATGGA AGCTGAAGTT TAATTCAGCT    4553
```

|   |   |   |   |   |      |
|---|---|---|---|---|------|
| GAGCGCTTGC | CCCTTTCCAA | CCTGGTTTCT | TTTTGTTCCT | TGAGTCCAGT | CAGAATGCCA | 4613 |
| TTCCCTGGCC | AGCAGCCAGC | CTTTAGTGAC | TGTCTCTGTT | CTGCAAAGCT | CTGTATATAG | 4673 |
| TTACTGAGTT | TCTGCAGGGG | GTGATCTTTG | CTCTTGTCCT | AAGAAATAAC | TACAGTGTTT | 4733 |
| TAAGAAATAT | TTGAGGCCGG | GTGCAGTGGT | TCACACCTGT | AATCCAGCAC | TTTGGGAGGC | 4793 |
| CAAGGCAGGT | GGATCATGAG | GTCAAGAGTT | TGAGACCATC | ATGGCCAACA | TGGTGAAACC | 4853 |
| CCATCTCTAC | TAAAAATACA | AAAATTAGCT | GGGTGTGGTG | GCGGGCACCT | GTAGTCCCAG | 4913 |
| CTACTCGGGA | GGCTGAGGCA | GGAGAATCGC | TTGAGCCTGG | GAGGCGGAGG | TTGCACTGAG | 4973 |
| CCGATATCAC | GCCACTGCAC | TCCAGCCTGG | CGACAGAGCG | AGACTCCATC | TCAAAAAAA | 5033 |
| GAAAAAATAA | ATAGTTGAAA | TAAAGACTGC | ACATAAAGAC | AAAAAAAAG | TTTATAAAGT | 5093 |
| TAAAAAATAA | AATAAAAAAC | AGGCTCCAGG | CTGGATTGGG | CCCAGAGGCT | GTAGGACACA | 5153 |
| GACCCCCAGC | CAATGACTTC | ATAAATCCGG | ATGTTAATCA | GCCTCACCTG | GGAATTTGGG | 5213 |
| GAGGGACTC | ATTTTAAAAC | AGTTTCCTGG | ATTCTAACCC | AACCCAGAAA | ATCAGACTCT | 5273 |
| TTGAGCTAAA | TTCTTAAGCT | CCCTGGTGAT | GATGATGGAA | CCAGTTTATG | GCTGACCCA | 5333 |
| GAGTACCGTC | TGAAAGACGT | GCCACATCCC | TCTCTCTCCA | GCCTCCCCTT | CTCCTCCATT | 5393 |
| CCCCAGGGAG | AATTC      |            |            |            |            | 5408 |

(2) INFORMATION FOR SEQ ID NO:21:

(i) SEQUENCE CHARACTERISTICS:
        (A) LENGTH: 88 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:21:

```
Met Ala Ser Gly Gln Gly Pro Gly Pro Pro Arg Gln Glu Cys Gly Lys
 1               5                  10                  15
Pro Ala Leu Pro Ser Ala Ser Glu Glu Gln Val Ala Gln Asp Met Glu
            20                  25                  30
Gly Phe Ser Ala Ala Thr Phe Phe Thr Thr Ile Ser Arg Asn Arg Arg
        35                  40                  45
Leu Lys Gly Arg Pro Pro Leu Pro Thr Gln Arg Trp Ser Pro Cys Pro
 50                  55                  60
Ser Asn Leu Ala Ala Pro Trp Gly Arg Trp Asp Gly Ser Ser Pro Ser
65                  70                  75                  80
Pro Gly Arg His Gln Pro Ala Leu
                85
```

(2) INFORMATION FOR SEQ ID NO:22:

(i) SEQUENCE CHARACTERISTICS:
        (A) LENGTH: 152 amino acids
        (B) TYPE: amino acid
        (C) STRANDEDNESS: single
        (D) TOPOLOGY: linear (xi) SEQUENCE DESCRIPTION: SEQ ID NO:22:

```
Met Val Thr Leu Pro Leu Gln Pro Ser Ser Thr Met Gly Gln Val Gly
 1               5                  10                  15
Arg Gln Leu Ala Ile Ile Gly Asp Asp Ile Asn Arg Arg Tyr Asp Ser
            20                  25                  30
```

```
Glu  Phe  Gln  Thr  Met  Leu  Gln  His  Leu  Gln  Pro  Thr  Ala  Glu  Asn  Ala
      35                      40                     45

Tyr  Glu  Tyr  Phe  Thr  Lys  Ile  Ala  Thr  Ser  Leu  Phe  Glu  Ser  Gly  Ile
 50                      55                     60

Asn  Trp  Gly  Arg  Val  Val  Ala  Leu  Leu  Gly  Phe  Gly  Tyr  Arg  Leu  Ala
 65                      70                     75                          80

Leu  His  Val  Tyr  Gln  His  Gly  Leu  Thr  Gly  Phe  Leu  Gly  Gln  Val  Thr
                85                      90                          95

Arg  Phe  Val  Val  Asp  Phe  Met  Leu  His  His  Cys  Ile  Ala  Arg  Trp  Ile
               100                     105                     110

Ala  Gln  Arg  Gly  Gly  Trp  Val  Ala  Ala  Leu  Asn  Leu  Gly  Asn  Gly  Pro
               115                     120                     125

Ile  Leu  Asn  Val  Leu  Val  Val  Leu  Gly  Val  Val  Leu  Leu  Gly  Gln  Phe
          130                     135                     140

Val  Val  Arg  Arg  Phe  Phe  Lys  Ser
145                     150
```

(2) INFORMATION FOR SEQ ID NO:23:

(i) SEQUENCE CHARACTERISTICS:
        (A) LENGTH: 141 amino acids
        (B) TYPE: amino acid
        (C) STRANDEDNESS: single
        (D) TOPOLOGY: linear (xi) SEQUENCE DESCRIPTION: SEQ ID NO:23:

```
Met  Gly  Gln  Val  Gly  Arg  Gln  Leu  Ala  Ile  Ile  Gly  Asp  Asp  Ile  Asn
 1                       5                      10                          15

Arg  Arg  Tyr  Asp  Ser  Glu  Phe  Gln  Thr  Met  Leu  Gln  His  Leu  Gln  Pro
                20                      25                          30

Thr  Ala  Glu  Asn  Ala  Tyr  Glu  Tyr  Phe  Thr  Lys  Ile  Ala  Thr  Ser  Leu
           35                      40                          45

Phe  Glu  Ser  Gly  Ile  Asn  Trp  Gly  Arg  Val  Val  Ala  Leu  Leu  Gly  Phe
      50                      55                          60

Gly  Tyr  Arg  Leu  Ala  Leu  His  Val  Tyr  Gln  His  Gly  Leu  Thr  Gly  Phe
 65                      70                          75                      80

Leu  Gly  Gln  Val  Thr  Arg  Phe  Val  Val  Asp  Phe  Met  Leu  His  His  Cys
                85                      90                          95

Ile  Ala  Arg  Trp  Ile  Ala  Gln  Arg  Gly  Gly  Trp  Val  Ala  Ala  Leu  Asn
               100                     105                     110

Leu  Gly  Asn  Gly  Pro  Ile  Leu  Asn  Val  Leu  Val  Val  Leu  Gly  Val  Val
          115                     120                     125

Leu  Leu  Gly  Gln  Phe  Val  Val  Arg  Arg  Phe  Phe  Lys  Ser
          130                     135                     140
```

(2) INFORMATION FOR SEQ ID NO:24:

(i) SEQUENCE CHARACTERISTICS:
        (A) LENGTH: 116 amino acids
        (B) TYPE: amino acid
        (C) STRANDEDNESS: single
        (D) TOPOLOGY: linear (xi) SEQUENCE DESCRIPTION: SEQ ID NO:24:

```
Met  Leu  Gln  His  Leu  Gln  Pro  Thr  Ala  Glu  Asn  Ala  Tyr  Glu  Tyr  Phe
 1                       5                      10                          15

Thr  Lys  Ile  Ala  Thr  Ser  Leu  Phe  Glu  Ser  Gly  Ile  Asn  Trp  Gly  Arg
                20                      25                          30

Val  Val  Ala  Leu  Leu  Gly  Phe  Gly  Tyr  Arg  Leu  Ala  Leu  His  Val  Tyr
```

|   |   |   | 35 |   |   |   | 40 |   |   |   | 45 |   |   |   |
|---|---|---|---|---|---|---|---|---|---|---|---|---|---|---|
| Gln | His 50 | Gly | Leu | Thr | Gly | Phe 55 | Leu | Gly | Gln | Val | Thr 60 | Arg | Phe | Val | Val |
| Asp 65 | Phe | Met | Leu | His | His 70 | Cys | Ile | Ala | Arg | Trp 75 | Ile | Ala | Gln | Arg | Gly 80 |
| Gly | Trp | Val | Ala | Ala 85 | Leu | Asn | Leu | Gly | Asn 90 | Gly | Pro | Ile | Leu | Asn 95 | Val |
| Leu | Val | Val | Leu 100 | Gly | Val | Val | Leu | Leu 105 | Gly | Gln | Phe | Val | Val 110 | Arg | Arg |
| Phe | Phe | Lys 115 | Ser |

APOPTOSIS-MODULATING PROTEINS, DNA ENCODING THE PROTEINS AND METHODS OF USE THEREOF

This application is a divisional of application Ser. No. 08/320,157 filed Oct. 7, 1994, which is a continuation-in-part of United States patent application Ser. No. 08/160,067 filed Nov. 30, 1993 now abandoned.

FIELD OF THE INVENTION

This invention relates to novel proteins with apoptosis-modulating activity, recombinant DNA encoding the proteins, compositions containing the proteins and methods of use thereof.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation and infection by human immunodeficiency virus (HIV). Wyllie (1980) Nature, 284:555–556; Kanter et al. (1984) Biochem. Biophys. Res. Commun. 118:392–399; Duke and Cohen (1986) Lymphokine Res. 5:289–299; Tomei et al. (1988) Biochem. Biophys. Res. Commun. 155:324–331; Kruman et al. (1991) J. Cell. Physiol. 148:267–273; Ameisen and Capron (1991) Immunology Today 12:102; and Sheppard and Ascher (1992) J. AIDS 5:143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) FASEB J. 6:2450; and Cohen and Duke (1992) Ann. Rev. Immunol. 10:267. The blebs, small, membrane-encapsulated spheres that pinch off of the surface of apoptotic cells, may continue to produce superoxide. radicals which damage surrounding cell tissue and may be involved in inflammatory processes.

Bcl-2 was discovered at the common chromosomal translocation site t(14:18) in follicular lymphomas and results in aberrant over-expression of bcl-2. Tsujimoto et al. (1984) Science 226:1097–1099; and Cleary et al. (1986) Cell 47:19–28. The normal function of bcl-2 is the prevention of apoptosis; unregulated expression of bcl-2 in B cells is thought to lead to increased numbers of proliferating B cells which may be a critical factor in the development of lymphoma. McDonnell and Korsmeyer (1991) Nature 349:254–256; and, for review see, Edgington (1993) Bio/Tech. 11:787–792. Bcl-2 is also capable of blocking of γ irradiation-induced cell death. Sentman et al. (1991) Cell 67:879–888; and Strassen (1991) Cell 67:889–899. It is now known that bcl-2 inhibits most types of apoptotic cell death and is thought to function by regulating an antioxidant pathway at sites of free radical generation. Hockenbery et al. (1993) Cell 75:241–251.

While apoptosis is a normal cellular event, it can also be induced by pathological conditions and a variety of injuries. Apoptosis is involved in a wide variety of conditions including but not limited to, cardiovascular disease, cancer regression, immunoregulation, viral diseases, anemia, neurological disorders, gastrointestinal disorders, including but not limited to, diarrhea and dysentery, diabetes, hair loss, rejection of organ transplants, prostate hypertrophy, obesity, ocular disorders, stress and aging.

Bcl-2 belongs to a family of proteins some of which have been cloned and sequenced. Williams and Smith (1993) Cell 74:777–779. All references cited herein, both supra and infra, are hereby incorporated by reference herein.

SUMMARY OF THE INVENTION

Substantially purified DNA encoding novel bcl-2 homologs, termed cdn-1, cdn-2 and cdn-3, as well as recombinant cells and transgenic animals expressing the cdn-1 and cdn-2 genes are provided. The substantially purified CDN-1 and CDN-2 proteins and compositions thereof are also provided. Diagnostic and therapeutic methods utilizing the DNA and proteins are also provided. Methods of screening for pharmaceutical agents that stimulate, as well as pharmaceutical agents that inhibit cdn-1 and cdn-2 activity levels are also provided.

BRIEF DESCRIPTION OF THE DRAWINGS

FIG. 1 (SEQ ID: 1 through SEQ ID NO: 5) depicts the PCR primers used to isolate the cdn-1 probes.

FIG. 2 depicts the cdn-1 clones obtained by the methods described in Example 1.

FIG. 3 (SEQ ID NO: 6 and SEQ ID NO: 7) depicts the nucleotide sequence of cdn-1 and the corresponding predicted amino acid sequence of the CDN-1 protein.

FIG. 5 (SEQ ID NO: 8 through SEQ ID NO: 9) shows the sequence of the cdn-2 cDNA and flanking sequences and the corresponding predicted amino acid sequence of the cdn-2 protein.

FIG. 6. (SEQ ID NO: 10 through SEQ ID NO: 19) shows a comparison of N-terminal amino acid sequences of cdn-1, cdn-2 and known bcl-2 family members.

FIG. 7 (SEQ ID NO: 20 and SEQ ID NO: 21) shows the nucleotide sequence of cdn-3 and the corresponding predicted amino acid sequence of the CDN-3 protein.

FIG. 11 (SEQ ID NO: 7) depicts the cdn-1 derivative proteins Δ1 (SEQ ID NO: 22), Δ2 (SEQ ID NO: 23) and Δ3 (SEQ ID NO: 24). The N-terminal residues are indicated by the arrows. The remainder of the derivative proteins is the same as full-length cdn-1.

DETAILED DESCRIPTION OF THE INVENTION

The present invention encompasses substantially purified nucleotide sequences encoding the novel bcl-2 homologs, cdn-1 and cdn-2; and the proteins encoded thereby; compositions comprising cdn-1 and cdn-2 genes and proteins and methods of use of thereof. Note that in copending United States patent application Ser. No. 08/160,067, cdn-1 was termed cdi-1; although the name has been changed, the nucleotide sequence remains identical. The invention further includes recombinant cells and transgenic animals expressing the cloned cdn-1 or cdn-2 genes. The nucleotide and predicted amino acid residue sequences of cdn-1 are shown in FIG. 3; and those of cdn-2 are shown in FIG. 5. It has now been found that the proteins encoded by the cdn genes are capable of modulating apoptosis. In a lymphoblastoid cell line, cdn-1 was shown to decrease Fas-mediated apoptosis. In a mouse progenitor B cell line, FL5.12, cdn-2 and a derivative of cdn-1 decrease IL-3-induced apoptosis whereas cdn-1 slightly increased apoptosis. Thus, depending on the cell type, the derivative of cdn and the method of induction of apoptosis, apoptosis can be modulated in a highly specific manner by controlling the concentration of cdns.

Figure 4:
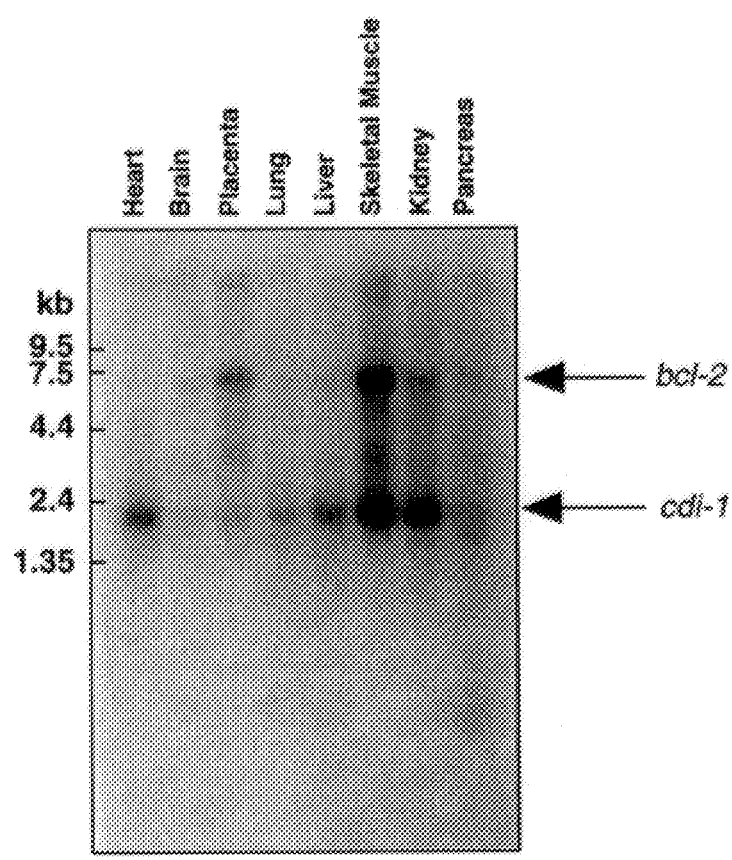
FIG. 4 depicts the results of a Northern blot analysis of multiple tissues with probes specific for both bcl-2 and cdn-1.

As used herein, "cdns" or "cdn" refers to the nucleic acid molecules described herein (cdn-1, cdn-2, cdn-3 and derivatives thereof), "the CDNs" or "CDN" refers to the proteins encoded thereby (CDN-1, CDN-2, CDN-3 and derivatives thereof). The present invention encompasses cdn-1 and cdn-2 nucleotide sequences. The cdn nucleotides include, but are not limited to, the cDNA, genome-derived DNA and synthetic or semi-synthetic DNA or RNA. The nucleotide sequence of the cdn-1 cDNA with the location of restriction endonuclease sites is shown in FIG. 3. As described in the examples herein, cdn-1 mRNA has been detected in a variety of human organs and tissues by Northern blot analysis. These organs include liver; heart; skeletal muscle; lung; kidney; and pancreas as shown in FIG. 4.

Similarly, cdn-2, cdn cDNA, genomic DNA and synthetic or semi-synthetic DNAs and RNAs are additional embodiments of the present invention. The nucleotide sequence of cdn-2 CDNA, along with the predicted amino acid sequence of cdn-2 protein and the locations-of restriction endonuclease recognition sites, is given in FIG. 5. The examples presented herein indicate that cdn-1 is on human chromosome 6 and that cdn-2 is on human chromosome 20. There is also a member of the family cdn-3 which is on human chromosome 11. Fluorescence in situ hybridization (FISH) indicated an approximate location of cdn-1 to be at 6p21–23. Within this region resides the gene for spinocerebellar ataxia type 1. Interestingly, apoptosis has been proposed recently to be involved in the related genetic disorder ataxia telangiectasia. Taken together with the chromosomal localization and the expression of cdn-1 in brain tissue, this suggests the possibility that cdn-1/cdn-2 might represent the SCAL gene locus. It is possible that cdn-2 and cdn-3 are pseudogenes. While these may not be expressed endogenously, they are capable of expression from a recombinant vector providing the appropriate promoter sequences. Thus, both cdn-2 and cdn-3 genes are encompassed by the present invention as are recombinant constructs thereof and proteins encoded thereby.

Derivatives of the genes and proteins include any portion of the protein, or gene encoding the protein, which retains apoptosis modulating activity. FIG. 11 depicts three such derivatives of cdn-1 which have been shown to retain apoptosis-modulating activity. These derivatives, cdnl-Δ1, cdnl-Δ2 and cdnl-Δ3, are encompassed by the present invention.

The invention includes modifications to cdn DNA sequences such as deletions, substitutions and additions particularly in the non-coding regions of genomic DNA. Such changes are useful to facilitate cloning and modify gene expression.

Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses functionally equivalent variants and derivatives of cdns which may enhance, decrease or not significantly affect the properties of CDNs. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of CDNs is encompassed by the present invention.

Techniques for nucleic acid manipulation useful for the practice of the present invention are described in a variety of references, including but not limited to, *Molecular Cloning: A Laboratory Manual,* 2nd ed., Vol. 1–3, eds. Sambrook et al. Cold Spring Harbor Laboratory Press (1989); and *Current Protocols in Molecular Bioloqy*, eds. Ausubel et al., Greene Publishing and Wiley-Interscience: New York (1987) and periodic updates.

The invention further embodies a variety of DNA vectors having cloned therein the cdn nucleotide sequences encoding. Suitable vectors include any known in the art including, but not limited to, those for use in bacterial, mammalian, yeast and insect expression systems. Specific vectors are known in the art and need not be described in detail herein.

The vectors may also provide inducible promoters for expression of the cdns. Inducible promoters are those which do not allow constitutive expression of the gene but rather, permit expression only under certain circumstances. Such promoters may be induced by a variety of stimuli including, but not limited to, exposure of a cell containing the vector to a ligand, metal ion, other chemical or change in temperature.

These promoters may also be cell-specific, that is, inducible only in a particular cell type and often only during a specific period of time. The promoter may further be cell cycle specific, that is, induced or inducible only during a particular stage in the cell cycle. The promoter may be both cell type specific and cell cycle specific. Any inducible promoter known in the art is suitable for use in the present invention.

The invention further includes a variety of expression systems transfected with the vectors. Suitable expression systems include but are not limited to bacterial, mammalian, yeast and insect. Specific expression systems and the use thereof are known in the art and are not described in detail herein.

The invention encompasses ex vivo transfection with cdns, in which cells removed from animals including man are transfected with vectors encoding CDNs and reintroduced into animals. Suitable transfected cells include individual cells or cells contained within whole tissues. In addition, ex vivo transfection can include the transfection of cells derived from an animal other than the animal or human subject into which the cells are ultimately introduced. Such grafts include, but are not limited to, allografts, xenografts, and fetal tissue transplantation.

Essentially any cell or tissue type can be treated in this manner. Suitable cells include, but are not limited to, cardiomyocytes and lymphocytes. For instance, lymphocytes, removed, transfected with the recombinant DNA and reintroduced into an HIV-positive patient may increase the half-life of the reintroduced T cells.

As an example, in treatment of HIV-infected patients by the above-described method, the white blood cells are removed from the patient and sorted to yield the CD4$^+$ cells. The CD4$^+$ cells are then transfected with a vector encoding CDNs and reintroduced into the patient. Alternatively, the unsorted lymphocytes can be transfected with a recombinant vector having at least one cdn under the control of a cell-specific promoter such that only CD4$^+$ cells express the cdn genes. In this case, an ideal promoter would be the CD4 promoter; however, any suitable CD4$^+$ T cell-specific promoter can be used.

Further, the invention encompasses cells transfected in vivo by the vectors. Suitable methods of in vivo transfection are known in the art and include, but are not limited to, that described by Zhu et al. (1993) Science 261:209–211. In vivo transfection by cdns may be particularly useful as a prophylactic treatment for patients suffering from atherosclerosis. Elevated modulation of the levels of CDN could serve as a prophylaxis for the apoptosis-associated reperfusion damage that results from cerebral and myocardial infarctions. In these patients with a high risk of stroke and heart attack, the apoptosis and reperfusion damage associated with arterial obstruction could be prevented or at least mitigated.

Infarctions are caused by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs to tissues surrounding the infarct upon reperfusion of blood to the area; thus, modulation of CDN levels, achieved by a biological modifier-induced change in endogenous production or by in vivo transfection, could be effective at reducing the severity of damage caused by heart attacks and stroke.

Transgenic animals containing the recombinant DNA vectors are also encompassed by the invention. Methods of making transgenic animals are known in the art and need not be described in detail herein. For a review of methods used to make transgenic animals, see, e.g. PCT publication no. WO 93/04169. Preferably, such animals express recombinant cdns under control of a cell-specific and, even more preferably, a cell cycle specific promoter.

In another embodiment, diagnostic methods are provided to detect the expression of cdns either at the protein level or the mRNA level. Any antibody that specifically recognizes CDNs is suitable for use in CDN diagnostics. Abnormal levels of CDNs are likely to be found in the tissues of patients with diseases associated with inappropriate apoptosis; diagnostic methods are therefore useful for detecting and monitoring biological conditions associated with such apoptosis defects. Detection methods are also useful for monitoring the success of CDN-related therapies.

Purification or isolation of CDNs expressed either by the recombinant DNA or from biological sources such as tissues can be accomplished by any method known in the art. Protein purification methods are known in the art. Generally, substantially purified proteins are those which are free of other, contaminating cellular substances, particularly proteins. Preferably, the purified CDNs are more than eighty percent pure and most preferably more than ninety-five percent pure. For clinical use as described below, the CDNs are preferably highly purified, at least about ninety-nine percent pure, and free of pyrogens and other contaminants.

Suitable methods of protein purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

The invention also includes the substantially purified CDNs having the amino acid residue sequences depicted in FIGS. 3 and 5, respectively. The invention encompasses functionally equivalent variants of CDNs which do not significantly affect their properties and variants which retain the same overall amino acid sequence but which have enhanced or decreased activity. For instance, conservative substitutions of amino acid residues, one or a few amino acid deletions or additions, and substitution of amino acid residues by amino acid analogs are within the scope of the invention.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of CDNs is encompassed by the present invention.

Suitable antibodies are generated by using the CDNs as an antigen or, preferably, peptides encompassing the CDN regions that lack substantial homology to the other gene products of the bcl family. Methods of detecting proteins using antibodies and of generating antibodies using proteins or synthetic peptides are known in the art and are not described in detail herein.

CDN protein expression can also be monitored by measuring the level of cdn mRNA. Any method for detecting specific mRNA species is suitable for use in this method. This is easily accomplished using the polymerase chain reaction (PCR). Preferably, the primers chosen for PCR correspond to the regions of the cdn genes which lack substantial homology to other members of the bcl gene family. Alternatively, Northern blots can be utilized to detect cdn mRNA by using probes specific to cdns. Methods of utilizing PCR and Northern blots are known in the art and are not described in detail herein.

Methods of treatment with cdns also include modulating cellular expression of cdns by increasing or decreasing levels of cdn MRNA or protein. Suitable methods of increasing cellular expression of cdn include, but are not limited to, increasing endogenous expression and transfecting the cells with vectors encoding cdns. Cellular transfection is discussed above and is known in the art. Suitable indications for increasing endogenous levels of cdn include, but are not limited to, malignancies and cardiac-specific over-expression. Cardiac specific over-expression is particularly suitable for use in indications including, but not limited to, patients susceptible to heart disease and in advance of cardiotoxic therapies including, but not limited to, chemotherapies such as adriamycin, so as to offer cardioprotection.

In addition, increasing endogenous expression of cdns can be accomplished by exposing the cells to biological modifiers that directly or indirectly increase levels of CDNs either by increasing expression or by decreasing degradation of cdn mRNA. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are exposed to such biological modifiers at physiologically effective concentrations, and the expression of cdns is measured relative to a control not exposed to the biological modifiers. Those biological modifiers which increase expression of cdns relative to the control are selected for further study.

The invention further encompasses a method of decreasing endogenous levels of cdns. The methods of decreasing endogenous levels of cdns include, but are not limited to, antisense nucleotide therapy and down-regulation of expression by biological modifiers. Antisense therapy is known in the art and its application will be apparent to one of skill in the art.

Screening for therapeutically effective biological modifiers is done by exposing the cells to biological modifiers which may directly or indirectly decrease levels of CDNs either by decreasing expression or by increasing the half-life of cdn mRNA or CDNs. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are grown under conditions known to elicit expression of at least one cdn (preferably cdn-1), exposed to such biological modifiers at physiologically effective concentrations, and the expression of cdns is measured relative to a control not exposed to biological modifiers. Those biological modifiers which decrease the expression of cdns relative to a control are selected for further study. Cell viability is also monitored to ensure that decreased cdn expression is not due to, cell death.

In determining the ability of biological modifiers to modulate (increase or decrease) cdn expression, the levels of endogenous expression may be measured or the levels of recombinant fusion proteins under control of cdn-specific promoter sequences may be measured. The fusion proteins are encoded by reporter genes.

Reporter genes are known in the art and include, but are not limited to chloramphenicol acetyl transferase (CAT) and β-galactosidase. Expression of cdn-1 and -2 can be monitored as described above either by protein or mRNA levels. Expression of the reporter genes can be monitored by enzymatic assays, or antibody-based assays, like ELISAs and RIAs, also known in the art. Potential pharmaceutical agents can be any therapeutic agent or chemical known to the art, or any uncharacterized compounds derived from natural sources such as fungal broths and plant extracts. Preferably, suitable pharmaceutical agents are those lacking substantial cytotoxicity and carcinogenicity.

Suitable indications for modulating endogenous levels of cdns are any in which cdn-mediated apoptosis is involved. These include, but are not limited to, various types of malignancies and other disorders resulting in uncontrolled cell growth such as eczema, or deficiencies in normal programmed cell death such as malignancies, including, but not limited to, B cell lymphomas.

The invention also encompasses therapeutic methods and compositions involving treatment of patients with biological modifiers to increase or decrease expression of cdns. Effective concentrations and dosage regimens may be empirically derived. Such derivations are within the skill of those in the art and depend on, for instance, age, weight and gender of the patient and severity of the disease. Alternatively, patients may be directly treated with either native or recombinant CDNs. The CDNs should be substantially pure and free of pyrogens. It is preferred that the recombinant CDNs be produced in a mammalian cell line so as to ensure proper glycosylation. CDNs may also be produced in an insect cell line and will be glycosylated.

For therapeutic compositions, a therapeutically effective amount of substantially pure CDN is suspended in a physiologically accepted buffer including, but not limited to, saline and phosphate buffered saline (PBS) and administered to the patient. Preferably administration is intravenous. Other methods of administration include but are not limited to, subcutaneous, intraperitoneal, gastrointestinal and directly to a specific organ, such as intracardiac, for instance, to treat cell death related to myocardial infarction.

Suitable buffers and methods of administration are known in the art. The effective concentration of a CDN will need to be determined empirically and will depend on the type and severity of the disease, disease progression and health of the patient. Such determinations are within the skill of one in the art.

Bcl-2 is thought to function in an antioxidant pathway. Veis et al. (1993) Cell 75:229–240. Therefore, therapy involving CDNs is suitable for use in conditions in which superoxide is involved. Administration of CDNs results in an increased extracellular concentration of CDNs, which is thought to provide a method of directly inhibiting superoxide accumulation that may be produced by the blebs associated with apoptosis. The therapeutic method thus includes, but is not limited to, inhibiting superoxide mediated cell injury.

Suitable indications for therapeutic use of CDNs are those involving free radical mediated cell death and include, but are not limited to, conditions previously thought to be treatable by superoxide dismutase. Such indications include but are not limited to HIV infection, autoimmune diseases, cardiomyopathies, neuronal disorders, hepatitis and other liver diseases, osteoporosis, and shock syndromes, including, but not limited to, septicemia.

Hybridization of cloned cdn DNA to messenger mRNA from various regions of the brain indicated high levels of expression of cdn-1 in each of the regions studied (FIG. 4). Therefore, neurological disorders are another area in which therapeutic applications of CDNs may be indicated.

The following examples are provided to illustrate but not limit the present invention. Unless otherwise specified, all cloning techniques were essentially as described by Sambrook et al. (1989) and all reagents were used according to the manufacturer's instructions.

EXAMPLE 1

Identification and Cloning of cdn-1 cDNA

An amino acid sequence comparison of the six known bcl-2 family members (FIG. 6) revealed two regions with considerable sequence identity, namely amino acids 144–150 and 191–199. In an attempt to identify new bcl-2 family members, degenerate PCR primers based on sequences in these regions were designed (FIG. 1) and PCR was performed using human heart cDNA and human B lymphoblastoid cell line (WIL-2) cDNA. PCR was performed using the Hot Start/Ampliwax technique (Perkin Elmer Cetus). The final concentration of the PCR primers and the template cDNA were 4 μM and 0.1–0.2 ng/ml, respectively. The conditions for cDNA synthesis were identical to those for first strand cDNA synthesis of the cDNA library as described below. PCR was performed in a Perkin Elmer Cetus DNA Thermal Cycler according to the method described by Kiefer et al. (1991) *Biochem. Biophys. Res. Commun.* 176:219–225, except that the annealing and extension temperatures during the first 10 cycles were 36° C. Following PCR, samples were treated with 5 units of DNA polymerase I, Klenow fragment for 30 min at 37° C. and then fractionated by electrophoresis on a 7% polyacrylamide, 1×TBE (Tris/borate/EDTA) gel. DNA migrating between 170–210 base pars was excised from the gel, passively eluted for 16 hours with gentle shaking in 10 mM Tris-HCl pH 7.5, 1 mM EDTA (TE), purified by passage over an Elutip-D column (Schleicher and Schuell), ligated to the pCR-Script vector (Stratagene) and transformed into Escherichia coli strain XL1-Blue MRF (Stratagene). Plasmid DNA from transformants (white colonies) containing both the heart and WIL-2 PCR products was isolated using the Magic Miniprep DNA Purification System (Promega), and the DNA inserts were sequenced by the dideoxy chain termination method according to Sanger et al. (1977) *Proc. Natl. Acad. Sci. USA* 74:5463–5467 (USB, Sequenase version 2.0). DNA sequence analysis of the eleven heart PCR products revealed two sequences identical to bcl-x (Boise et al. (1993) *Cell* 74:597–608) and ten other sequences unrelated to the bcl-2 family.

DNA sequence analyses of the eleven WIL-2 PCR products yielded one bcl-x sequence, five sequences identical to another bcl-2 family member, bax (Oldvai et al. (1993) *Cell* 74:609–619), four unrelated sequences and one novel bcl-2 related sequence, termed cdn-1. The unique cdn-1 amino acid sequence encoded by the PCR product is shown in FIG. 6 from amino acid 151–190 (top row).

To isolate the cdn-1 cDNA, a human heart cDNA library (Clontech) and a WIL-2 cDNA library, constructed as described by Zapf et al. (1990) *J. Biol. Chem.* 265:14892–14898 were screened using the cdn-1 PCR DNA insert as a probe. The DNA was $^{32}$p-labeled according to the method described by Feinberg and Vogelstein (1984) *Anal. Biochem.* 137:266–267 and used to screen 150,000 recombinant clones from both libraries according to the method described by Kiefer et al. (1991). Eight positive clones from the WIL-2 cDNA library and two positive clones from the heart cDNA library were identified. Four clones from the WIL-2 cDNA library and two from the heart cDNA library were further purified and plasmid DNA containing the cDNA inserts was excised from the λZAPII vector (Stratagene) (FIG. 2). The two longest clones, W7 (2.1 kb) and W5 (2.0 kb) were sequenced and shown to contain the cdn-1 probe sequence, thus confirming their authenticity. The heart cDNAs also encoded cdn-1.

The W7 DNA sequence along with the deduced amino acid residue sequence is shown in FIG. 3. The deduced amino acid sequence of cdn-1 was also aligned for maximum sequence identity with the other bcl-2 family members and is shown in FIG. 6. As can be seen, there is considerable sequence identity between cdn-1 and other family members between amino acids 100 and 200. Beyond this central region, sequence conservation falls off sharply. Like bcl-2, cdn-1 appears to be an intracellular protein in that it does not contain either a hydrophobic signal peptide or N-linked glycosylation sites. Cdn-1 does contain a hydrophobic C-terminus that is also observed with all bcl-2 family members except LMW5-HL, suggesting its site of anti-apoptotic activity, like that of bcl-2, is localized to a membrane bound organelle such as the mitochondrial membrane, the endoplasmic reticulum or the nuclear membrane. Hockenbery et al. (1990); Chen-Levy et al. (1989) *Mol. Cell. Biol.* 9:701–710; Jacobsen et al. (1993) *Nature* 361:365–369; and Monighan et al. (1992) *J. Histochem. Cytochem.* 40:1819–1825.

EXAMPLE 2

Northern Blot Analysis of cDNA Clones

Northern blot analysis was performed according to the method described by Lehrach et al. (1977) *Biochem.* 16:4743–4651; and Thomas (1980) *Proc. Natl. Acad. Sci. USA* 77:5201–5205. In addition, a human multiple tissue Northern blot was purchased from Clontech. The coding regions of bcl-2 and cdn-1 cDNAs were labeled by the random priming method described by Feinberg and Vogelstein (1984) *Anal. Biochem.* 137:266–267. Hybridization and washing conditions were performed according to the methods described by Kiefer et al. (1991).

The results, presented in FIG. 4, indicate that cdn-1 is expressed in all organs tested (heart, brain, placenta, lung, liver, skeletal muscle, kidney and pancreas) whereas bcl-2 is not expressed or expressed at only low levels in heart, brain, lung, and liver. Thus, cdn-1 appears to be more widely expressed throughout human organs than bcl-2 and may be more important in regulating apoptosis in these tissues.

EXAMPLE 3

Expression of Recombinant cdn-1

In order to express recombinant cdn-1 in the baculovirus system, the cdn-1 cDNA generated in Example 1 was used to generate a novel cdn-1 vector, by a PCR methodology as described in Example 1, using primers from the 3' and 5' flanking regions of the gene which contain restriction sites to facilitate cloning. The plasmids were sequenced by the dideoxy terminator method (Sanger et al., 1977) using sequencing kits (USB, Sequenase version 2.0) and internal primers. This was to confirm that no mutations resulted from PCR.

A clone was used to generate recombinant viruses by in vivo homologous recombination between the overlapping sequences of the plasmid and AcNPV wild type baculovirus. After 48 hours post-transfection in insect Spodoptera frugiperda clone 9 (SF9) cells, the recombinant viruses were collected, identified by PCR and further purified. Standard procedures for selection, screening and propagation of recombinant baculovirus were performed (Invitrogen). The molecular mass, on sodium dodecyl sulfate-polyacrylamide gel electrophoresis (SDS-PAGE), of the protein produced in the baculovirus system was compared with the predicted molecular mass of cdn-1 according to the amino-acid sequence.

In addition, similar clones can be expressed, preferably in a yeast intracellular expression system, by any method known in the art, including the method described by Barr et al. (1992) *Transgenesis* ed. JAH Murray, (Wiley and Sons) pp. 55–79.

EXAMPLE 4

Expression of cdn-1 in Mammalian Systems

The cdn-1 coding sequence was excised from a plasmid generated in Example 1, and introduced into plasmids pCEP7, pREP7 and pcDNA3 (Invitrogen) at compatible restriction enzyme sites. pCEP7 was generated by removing the RSV 3'-LTR of pREP7 with XbaI/Asp718, and substituting the CMV promoter from pCEP4 (Invitrogen). 25 µg of each cdn-1-containing plasmid was electroporated into the B lymphoblastoid cell line WIL-2, and stable hygromycin resistant transformants or G418 resistant transformants (pcDNA3 constructs, FIG. 8) expressing cdn-1 were selected.

The coding region of cdns can also be ligated into expression vectors capable of stably integrating into other cell types including but not limited to cardiomyocytes, neural cell lines such as GTI-7 and TNF sensitive cells such as the human colon adenocarcinoma cell line HT29 so as to provide a variety of assay systems to monitor the regulation of apoptosis by cdn-1.

EXAMPLE 5

Effect of the Anti-Apoptotic Activity of cdn-1 and its Derivatives in the Wild Type B Lymphoblastoid Cell Line WIL2-729 HF2 and the Transformed Cell Expressing Excess cdn-1

$2 \times 10^5$ WIL-2, and WIL-2 cells transformed with a vector encoding cdn-1 as described in Example 4 were grown in RPMI supplemented with 10% fetal bovine serum (FBS) for the anti-fas experiment or 0.1% FBS for serum deprivation experiments. In the case of the anti-fas experiment, after washing with fresh medium, the cells were suspended in RPMI supplemented with 10% FBS, exposed to anti-fas antibodies and the kinetics of cell death in response to an apoptosis inducing agent were analyzed by flow cytometry with FACScan. In the case of the serum deprivation experiment, the WIL-2 cells were resuspended in RPMI supplemented with 0.1% FBS and apoptosis was monitored according to the method described by Henderson et al. (1993) *Proc. Natl. Acad. Sci. USA* 90:8479–8483. Other methods of inducing apoptosis include, but are not limited to, oxygen deprivation in primary cardiac myocytes, NGF withdrawal, glutathione depletion in the neural cell line GTI-7 or TNF addition to the HT29 cell line. Apoptosis was assessed by measuring cell shrinkage and permeability to propidium iodide (PI) during their death. In addition, any other method of assessing apoptotic cell death may be used.

Figure 8:
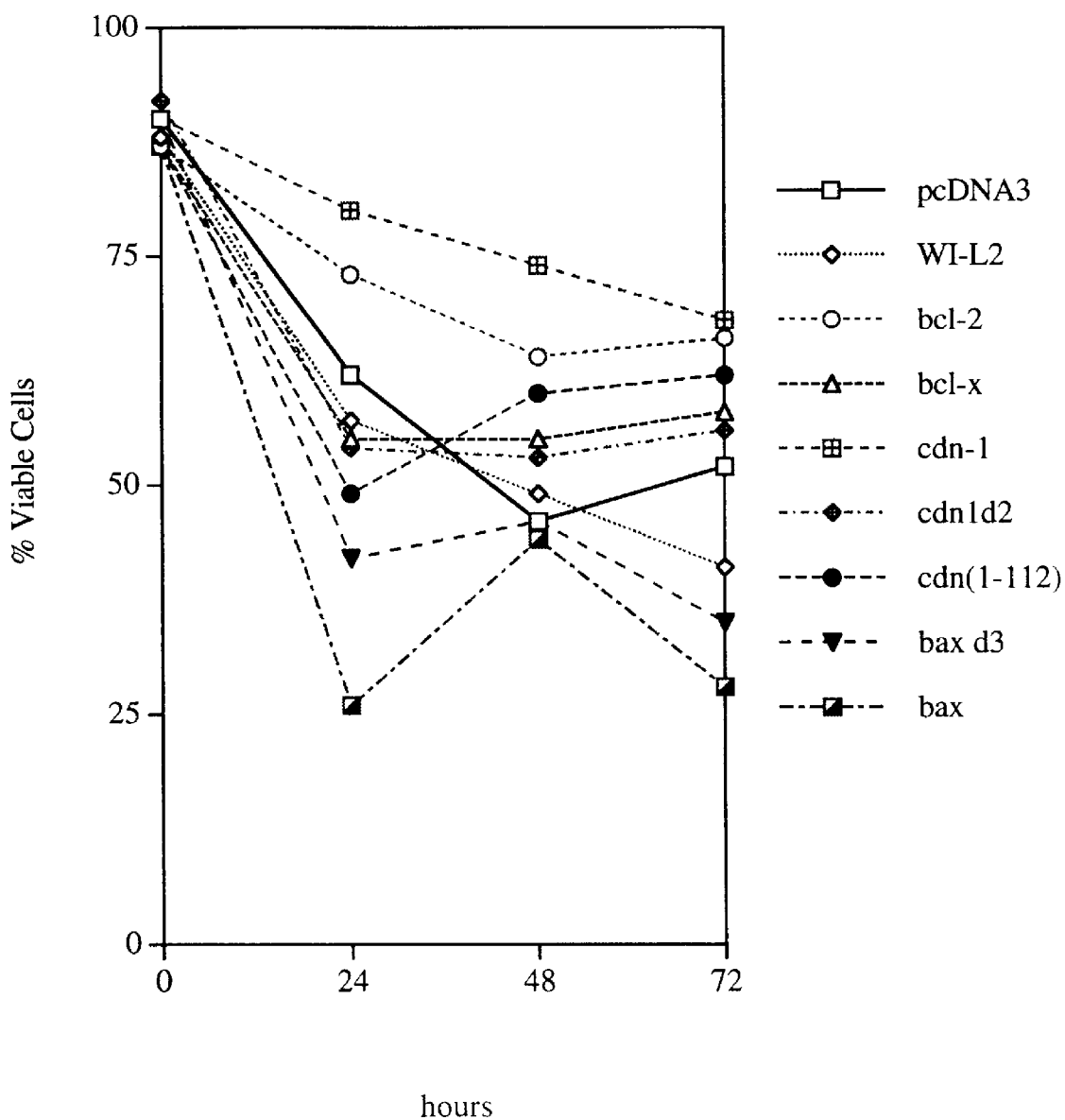
FIG. 8 shows the anti-apoptotic effects of cdn-1 and some of its derivatives in serum-deprivation induced apoptosis of WIL-2 cells.
Figure 9:
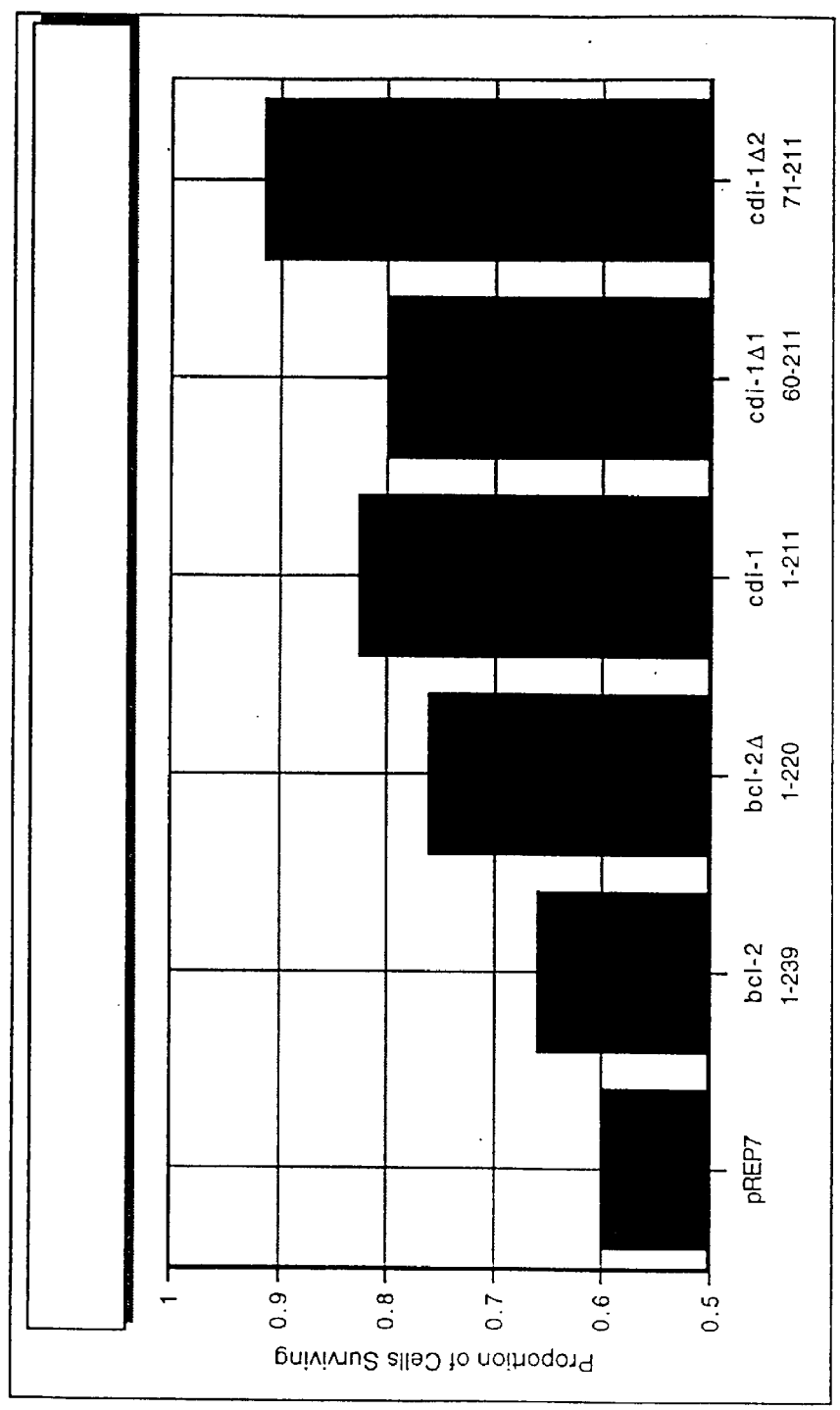
FIG. 9 shows anti-apoptotic effects of cdn-1 and some of its derivatives in FAS-induced apoptosis of WIL-2 cells.

FIG. 9 shows the anti-apoptotic response of various WIL-2 transformants to anti-Fas treatment. FIG. 8 shows the anti-apoptotic response of various WIL-2 transformants to serum deprivation. In FIG. 9, duplicate wells containing $3 \times 10^5$ cells were incubated with 50 ng/ml of the cytocidal anti-Fas antibody for 24 hours. Cell death was then analyzed by flow cytometry with FACScan. The proteins expressed from each construct are shown beneath the columns. Since many of the constructs are truncation or deletion variants, the exact amino acids expressed are also indicated. As can be seen, all of the transformants had some protective effect when compared to the control transformant containing the pREP7 vector alone. The most apoptosis-resistant transformant was the cdn-1Δ2 expressing cell line, in which over 90% of the cells survived anti-fas treatment. Significant protection was also observed in transformants expressing full length cdn-1 (1–211) and cdn-1Δ1, followed by bcl-2Δ and bcl-2 expressing cell lines.

Cdn-1Δ1 and cdn-1Δ2 are lacking the N-terminal 59 and 70 amino acids of the full length cdn-1 molecule, respectively. The observation that cdn-1Δ2 is more effective at blocking apoptosis than full length cdn-1 suggests that smaller, truncated cdn-1 molecules may be potent therapeutics.

EXAMPLE 6

Determination of other cdn genes and Cloning of the cdn-2 Gene

Southern blot analyses of human genome DNA and a panel of human/rodent somatic cell DNAs indicated that there were at least 3 cdn related genes and that they resided in chromosomes 6, 11 and 20. PCR/sequence analysis of the three hybrid DNAs showed that cdn-1 was on chromosome 6 and that two closely related sequences were on chromosome 20 (designated cdn-2) and chromosome 11 (designated cdn-3). We have cloned the cdn-2 and cdn-3 genes and sequenced them. Interestingly, both cdn-2 and cdn-3 do not contain introns and have all of the features of processed genes that have returned to the genome. cdn-3 has a nucleotide deletion, causing a frame shift and early termination and thus is probably a pseudogene. Both, however, have promoter elements upstream of the repeats CCAAT, TATAAA boxes but are probably not transcribed. (as determined by Northern blot analysis with cdn-2 and cdn-3 specific probes.)

900,000 clones from a human placenta genomic library in the cosmid vector pWE15 (Stratagene, La Jolla, Calif.) were screened with a 950 bp BglII-HindIII cDNA probe containing the entire coding region of Cdn-1. The probe was $^{32}$p-labeled according to the method of Feinberg and Vogelstein (1984). The library was processed and screened under high stringency hybridization and washing conditions as described by Sambrook et al. (1989) Molecular Cloning, 2nd edition, Cold Spring Harbor Laboratory Press. Ten double positive clones were further purified by replating and screening as above. Plasmid DNA was purified using the Wizard Maxiprep DNA Purification System as described by the supplier (Promega Corp., Madison, Wis.) and analyzed by EcoRI restriction enzyme mapping and Southern blotting. The probe used for Southern blotting and hybridization conditions was the same as above.

The cosmid clones fell into two groups as judged by EcoRI restriction analysis and Southern blotting. Cosmid clones (cos) 1–4 and 7 displayed one distinct pattern of EcoRI generated DNA fragments and contained a single 6.5 kb hybridizing EcoRI DNA fragment. Cos2 and Cos9 fell into the second group that was characterized by a 5.5 kb hybridizing EcoRI DNA fragment. The 6.5 kb DNA fragment from cos2 and the 5.5 kb DNA fragment from cos9 were subcloned into pBluescript SK (Stratagene, La Jolla, Calif.) using standard molecular biological techniques (Sambrook et al. as above). Plasmid DNA was isolated and the DNA inserts from two subclones, A4 (from cos2) and C5 (from cos9) were mapped with BamHI, HindIII and EcoRI and analyzed by Southern blotting as described above. Smaller restriction fragments from both clones were subcloned into M13 sequencing vectors and the DNA sequence was determined.

The sequence of A4 contains an open reading frame that displays 97% amino acid sequence identity with cdn-1. (FIG. 5) The high degree of sequence identity of this gene with cdn-1 indicates that it is a new cdn-1 related gene and therefore will be called cdn-2. A sequence comparison of the encoded cdn-2 protein and the other members of the bcl-2 family is shown in FIG. 6. Cdn-2 contains the conserved regions, BH1 and BH2, that are hallmarks of the bcl-2 family, and displays a lower overall sequence identity (~20–30%) to other members, which is also characteristic of the bcl-2 family. cdn-3 has a frame shift and therefore does not contain the structural features of cdn-1, cdn-2 or other bcl-2 family members.

EXAMPLE 7

Chromosomal Localization of the cdn-1 and cdn-2 Genes

Southern blot analysis of a panel of human/rodent somatic cell hybrid DNAs (Panel #2 DNA from the NIGMS, Camden, N.J.) and fluorescent in situ hybridization (FISH) of metaphase chromosomes were used to map the cdn genes to human chromosomes. For Southern blotting, 5 µg of hybrid panel DNA was digested with EcoRI or BamHI/HindIII, fractionated on 0.8% or 1% agarose gels, transferred to nitrocellulose and hybridized with the cdn-1 probe. Hybridization and washing conditions were as described above. For FISH, the cdn-2 subclone, A4, was biotinylated using the Bionick Labeling System (Gibco BRL, Gaithersburg, Md.) and hybridized to metaphase chromosomes from normal human fibroblasts according to the method described by Viegas-Pequignot in In Situ Hybridization, A Practical Approach, 1992, ed. D. G. Wilkinson, pp. 137–158, IRL Press, Oxford. Probe detection using FITC-conjugated avidin and biotinylated goat anti-avidin was according to the method described by Pinkel et al. (1988) *Proc. Natl. Acad. Sci. USA* 85:9138–9142.

Southern blot analysis showed three hybridizing EcoRI bands in the human DNA control that were approximately 12 kb, 11 kb and 5.5 kb in length. Analysis of the somatic cell hybrid DNA indicated that the 12 kb band was in two different samples, NA10629, which contained only human chromosome 6, and NA07299, which contained both human chromosomes 1 and X and, importantly, a portion of chromosome 6 telomeric to p21. The 11 kb band was in NA13140, which contains human chromosome 20. The 5.5 kb hybridizing band was found only in sample NA10927A, which contained human chromosome 11. PCR/DNA sequencing analysis of these hybrid DNA samples using primers for cdn-1 or cdn-2, showed cdn-1 sequences in NA10629 (the chromosome 6-containing hybrid DNA) and NA07299 (the chromosome 1, X and 6pter >p21-containing hybrid DNA), indicating that the cdn-1 gene resides on chromosome 6, telomeric to p21. cdn-2 sequences were found in NA13140, indicating the cdn-2 gene resides on chromosome 20, and cdn-3 sequences were found in NA10927A, indicating the cdn-3 gene resides on chromosome 11.

EXAMPLE 8

Modulation of apoptosis by cdn-1 and cdn-2 in FL5.12 cells

FL5.12 is an IL-3-dependent lymphoid progenitor cell line (McKearn et al. (1985) *Proc. Natl. Acad. Sci USA* 82:7414–7418) that has been shown to undergo apoptosis following withdrawal of IL-3 but is protected from cell death by overexpression of bcl-2. Nunez et al. (1990) *J. Immunol.* 144:3602–3610; and Hockenbery et al. (1990) *Nature* 348:334–336. To assess the ability of cdn-1 and cdn-2 to modulate apoptosis, cDNAs encoding cdn-1, cdn-2, two truncated forms of cdn-1 (described below) and bcl-2 were ligated into the mammalian expression vector, pcDNA3 (Invitrogen, San Diego, Calif.) and stably introduced into the mouse progenitor B lymphocyte cell line FL5.12 by electroporation and selection in media containing the antibiotic G418. Assays were then performed on bulk transformants as described below.

Figure 10:
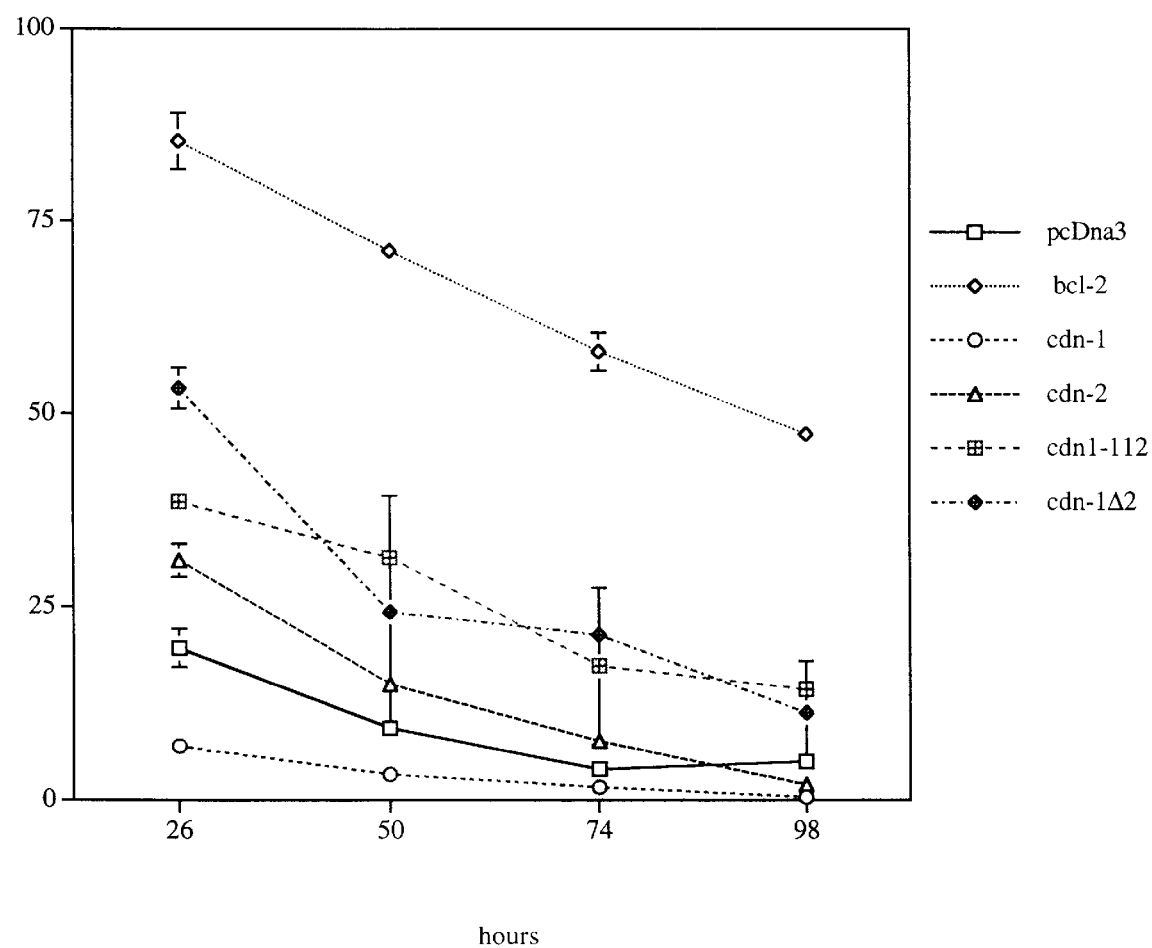
FIG. 10 shows modulation of apoptosis by cdn-1 and cdn-2 in FL5.12 cells.

The effects of the overexpressed genes on FL5.12 cell viability were examined at various times following withdrawal of IL-3 and are shown in FIG. 10. Cell viability was assessed by propidium iodide (PI) exclusion on a flow cytometer (Becton Dickinson FACScan). Bcl-2 expression protected the cells significantly from cell death while cdn-1 appeared to enhance cell death when compared to the vector control. Cdn-2 expression conferred a low level of protection from cell death at earlier times but was insignificant at later time points. Interestingly, cdn-1Δ2 gave a moderate level of protection against cell death. Cdn-1-112, a molecule that contains the N-terminal 112 amino acids of cdn-1, also appeared to partially protect the FL5.12 cells although at lower levels than Bcl-2.

As shown in Example 7, expression of cdn-1 and cdn-1Δ2 in WIL2 cells resulted in increased cell survival in response to anti-Fas-mediated apoptosis and serum withdrawal. Taken together, these data suggest that the various cdn molecules are capable of modulating apoptosis in a positive or negative manner, depending on the cell type and apoptotic stimuli. Thus, they are effective in preventing cell death such as in the post-ischemic reperfusion tissue damage in the heart or in inducing cell death in cells that have escaped apoptotic control, as is the case in various cancers.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

We claim:

1. An isolated nucleic acid molecule comprising a nucleotide sequence encoding the amino acid sequence of SEQ ID NO: 7 or the complement of said nucleotide sequence.

2. A composition comprising the nucleic acid molecule of claim 1.

3. An isolated nucleic acid molecule comprising a nucleotide sequence encoding the amino acid sequence of SEQ ID NO: 9 or the complement of said nucleotide sequence.

4. A composition comprising the nucleic acid molecule of claim 3.

5. An isolated nucleic acid molecule comprising a nucleotide sequence encoding the amino acid sequence of SEQ ID NO: 22 or the complement of said nucleotide sequence.

6. A composition comprising the nucleic acid molecule of claim 5.

7. An isolated nucleic acid molecule comprising a nucleotide sequence encoding the amino acid sequence of SEQ ID NO: 23 or the complement of said nucleotide sequence.

8. A composition comprising the nucleic acid molecule of claim 7.

9. An isolated nucleic acid molecule comprising a nucleotide sequence encoding the amino acid sequence of SEQ ID NO: 24 or the complement of said nucleotide sequence.

10. A composition comprising the nucleic acid molecule of claim 9.

11. A recombinant DNA vector comprising the nucleotide sequence of claim 1.

12. A composition comprising the recombinant DNA vector of claim 11.

13. A recombinant DNA vector comprising the nucleotide sequence of claim 3.

14. A composition comprising the recombinant DNA vector of claim 13.

15. A recombinant DNA vector comprising the nucleotide sequence of claim 5.

16. A composition comprising the recombinant DNA vector of claim 15.

17. A recombinant DNA vector comprising the nucleotide sequence of claim 7.

18. A composition comprising the recombinant DNA vector of claim 17.

19. A recombinant DNA vector comprising the nucleotide sequence of claim 9.

20. A composition comprising the recombinant DNA vector of claim 19.

21. The composition of claim 12, wherein said recombinant DNA vector is an expression vector and wherein transcription of said nucleotide sequence is under control of an inducible promoter.

22. The composition of claim 14, wherein said recombinant DNA vector is an expression vector and wherein transcription of said nucleotide sequence is under control of an inducible promoter.

23. The composition of claim 16, wherein said recombinant DNA vector is an expression vector and wherein transcription of said nucleotide sequence is under control of an inducible promoter.

24. The composition of claim 18, wherein said recombinant DNA vector is an expression vector and wherein transcription of said nucleotide sequence is under control of an inducible promoter.

25. The composition of claim 20, wherein said recombinant DNA vector is an expression vector and wherein transcription of said nucleotide sequence is under control of an inducible promoter.

26. A composition comprising a cell transfected with the recombinant DNA vector of claim 11.

27. A composition comprising a cell transfected with the recombinant DNA vector of claim 13.

28. A composition comprising a cell transfected with the recombinant DNA vector of claim 15.

29. A composition comprising a cell transfected with the recombinant DNA vector of claim 17.

30. A composition comprising a cell transfected with the recombinant DNA vector of claim 19.

\* \* \* \* \*